(12) United States Patent
Koscielski et al.

(10) Patent No.: US 11,986,434 B2
(45) Date of Patent: May 21, 2024

(54) MEDICAL WALKER

(71) Applicant: Enlighten Mobility, LLC, Columbus, OH (US)

(72) Inventors: Marissa C. Koscielski, South Bend, IN (US); Adrian Elias Rodriguez, South Bend, IN (US); Jeffrey Riney, Houston, TX (US); Vincent J. Contini, Powell, OH (US); Michael D. Milosh, Sunbury, OH (US)

(73) Assignee: Enlighten Mobility LLC, Columbus, OH (US)

( * ) Notice: Subject to any disclaimer, the term of this patent is extended or adjusted under 35 U.S.C. 154(b) by 0 days.

(21) Appl. No.: 16/220,116

(22) Filed: Dec. 14, 2018

(65) Prior Publication Data

US 2019/0183719 A1 Jun. 20, 2019

Related U.S. Application Data

(60) Provisional application No. 62/662,392, filed on Apr. 25, 2018, provisional application No. 62/599,057, filed on Dec. 15, 2017.

(51) Int. Cl.
*A61H 3/04* (2006.01)
*A61F 2/60* (2006.01)
(Continued)

(52) U.S. Cl.
CPC .............. *A61H 3/04* (2013.01); *A61F 2/60* (2013.01); *A61H 1/0237* (2013.01);
(Continued)

(58) Field of Classification Search
CPC ........ A61H 3/04; A61H 3/008; A61H 1/0237; A61H 1/0262; A61H 2003/005;
(Continued)

(56) References Cited

U.S. PATENT DOCUMENTS

| 4,697,808 A | 10/1987 | Larson et al. |
| 5,588,456 A | 12/1996 | Hart |

(Continued)

FOREIGN PATENT DOCUMENTS

| CN | 106334265 | 1/2017 |
| EP | 2907495 | 8/2015 |

(Continued)

OTHER PUBLICATIONS

Invacare Corporation, "Invacare Get-U-Up Hydraulic Stand-Up Lift", webpage, http://www.invacare.com/cgi-bin/imhqprd/inv_catalog/prod_cat_detail.jsp?prodID=GHS350, last accessed Mar. 31, 2019.

*Primary Examiner* — Keri J Nelson
*Assistant Examiner* — Aren Patel

(57) ABSTRACT

A medical walker apparatus and a method for using the medical walker. Embodiments of the medical walker include a wheeled frame and a compromised limb gait system attached to the wheeled frame, where the compromised limb gait system is configured to guide a limb of a user through a simulated gait motion. In aspects, the medical walker gives an amputee patient mobility by providing a leg brace support for the compromised limb with a flexible connection to the walker that guides the compromised limb through a biomechanically proper walking motion, thus allowing the compromised limb to be exercised.

19 Claims, 28 Drawing Sheets

(51) Int. Cl.
   *A61H 1/02* (2006.01)
   *A61H 3/00* (2006.01)
   *A63B 21/055* (2006.01)

(52) U.S. Cl.
   CPC .......... *A61H 1/0262* (2013.01); *A61H 3/008* (2013.01); *A61H 2003/005* (2013.01); *A61H 2003/006* (2013.01); *A61H 2003/007* (2013.01); *A61H 2201/1238* (2013.01); *A61H 2201/1253* (2013.01); *A61H 2201/1261* (2013.01); *A61H 2201/1621* (2013.01); *A61H 2201/163* (2013.01); *A61H 2201/1633* (2013.01); *A61H 2201/1635* (2013.01); *A61H 2201/1652* (2013.01); *A63B 21/0552* (2013.01)

(58) Field of Classification Search
   CPC ........ A61H 2003/006; A61H 2003/007; A61H 2201/1238; A61H 2201/1253; A61H 2201/1621; A61H 2201/163; A61H 2201/1633; A61F 2/60
   USPC .......................................................... 623/26
   See application file for complete search history.

(56) References Cited

U.S. PATENT DOCUMENTS

| | | | |
|---|---|---|---|
| 5,662,560 | A | 9/1997 | Svendsen |
| 5,702,326 | A | 12/1997 | Renteria |
| 5,728,164 | A | 3/1998 | Ferrari et al. |
| 5,766,236 | A | 6/1998 | Detty et al. |
| 6,343,802 | B1 | 2/2002 | Workman et al. |
| 6,607,202 | B1 | 8/2003 | Palmer |
| 6,645,126 | B1 | 11/2003 | Martin et al. |
| 6,652,427 | B2 * | 11/2003 | Wroclawsky .......... A63B 22/02 482/111 |
| 6,832,770 | B1 | 12/2004 | Wright-Ott et al. |
| 7,150,722 | B1 | 12/2006 | Tyrrell |
| 7,422,550 | B1 | 9/2008 | Pinero et al. |
| 8,905,951 | B2 | 12/2014 | Barriskill et al. |
| 9,370,680 | B1 | 6/2016 | Macaulay et al. |
| 9,415,205 | B2 | 8/2016 | Lasko et al. |
| 9,616,282 | B2 | 4/2017 | Tholkes et al. |
| 9,649,243 | B2 | 5/2017 | Johnson et al. |
| 9,662,526 | B2 | 5/2017 | Agrawal et al. |
| 10,076,656 | B2 | 9/2018 | Dar et al. |
| 10,376,734 | B1 | 8/2019 | Razon |
| 10,406,059 | B2 | 9/2019 | Agrawal et al. |
| 10,870,198 | B1 * | 12/2020 | Asbeck .................. A61H 1/02 |
| 2002/0010056 | A1 | 1/2002 | Borsheim |
| 2003/0093021 | A1 | 5/2003 | Goffer |
| 2004/0023759 | A1 | 2/2004 | Duncan et al. |
| 2010/0170546 | A1 | 7/2010 | Popovic et al. |
| 2012/0000496 | A1 | 1/2012 | Razon |
| 2014/0087922 | A1 | 3/2014 | Bayerlein et al. |
| 2015/0075575 | A1 * | 3/2015 | Karlovich ............... A61H 3/008 135/66 |
| 2015/0351995 | A1 * | 12/2015 | Zoss .................... A61H 1/0244 623/32 |
| 2016/0166454 | A1 * | 6/2016 | Johnson ............... A61H 9/0078 280/1.5 |
| 2016/0310731 | A1 | 10/2016 | Dixon et al. |
| 2016/0331626 | A1 * | 11/2016 | Fellingham ............. A61H 3/04 |
| 2018/0330817 | A1 | 11/2018 | Avni et al. |
| 2019/0015273 | A1 * | 1/2019 | Linon .................... A61G 5/068 |
| 2019/0046828 | A1 | 2/2019 | Kuehne et al. |
| 2019/0060154 | A1 * | 2/2019 | Lee ....................... A61H 1/0281 |
| 2019/0099315 | A1 | 4/2019 | Kuehne et al. |
| 2019/0216674 | A1 * | 7/2019 | Maggu .................. A61H 3/008 |
| 2019/0231632 | A1 * | 8/2019 | Hoekelmann ........... A61H 3/04 |
| 2019/0282431 | A1 * | 9/2019 | Moore ................. A61H 1/0237 |

FOREIGN PATENT DOCUMENTS

| | | |
|---|---|---|
| GB | 2484463 | 4/2012 |
| RU | 157028 U1 | 11/2015 |
| WO | WO2006118756 | 9/2006 |
| WO | WO 2014001853 | 3/2014 |
| WO | WO2014177206 | 11/2014 |

* cited by examiner

MEDICAL WALKER

CROSS-REFERENCE TO RELATED APPLICATIONS

This application claims the benefit of the filing date of U.S. provisional patent application Ser. No. 62/599,057, filed on Dec. 15, 2017, entitled "Medical Walker," of U.S. provisional patent application Ser. No. 62/662,392, filed on Apr. 25, 2018 entitled "Medical Walker," and the disclosures of which is incorporated herein by reference

BACKGROUND

Physical therapy and rehabilitation are long and difficult processes for patients with compromised limbs or unilateral immobility. Following surgery, amputation patients frequently do not receive adequate healthcare resources to meet their rehabilitation needs. Patients who have had a portion of one of their legs amputated wait, at a minimum, six to eight weeks for a prosthetic limb to be fabricated, and often the time required for the limb to heal and the prosthetic to be fabricated is much longer than that. During this waiting period, the vast majority of patients rely exclusively on a wheelchair for mobility. Similarly, patients with full or partial paralysis of a lower limb, or other conditions that result in a compromised lower limb, may be confined to a wheelchair during recovery. For weeks, patients are wheelchair-bound and thus not experiencing proper biomechanics, typical pelvic walking motions, or muscle activation. This wheelchair-bound immobility of the lower limbs can lead to irreversible physiological breakdowns with severe consequences, such as muscle atrophy, joint contractures, phantom limb syndrome, and acceleration of peripheral artery disease. Additionally, in cases where amputation was required because of a patient's vascular disease, the immobility can accelerate the vascular disease in the remaining, non-amputated limb leading to additional medical treatment. It is all too common for patient's that experience an illness or injury, such as a stroke or amputation, to undergo inpatient rehabilitation for a brief period, but then upon returning to their own home those patients experience a rapid decline because they do not have assistive technology for locomotor training.

Generally, amputation patients depend on wheelchairs, crutches, and walkers for ambulation and rehabilitation before a prosthetic device can be fabricated. Similarly, patients with monoplegia or stroke victims struggle with conventional wheelchairs, crutches, and walkers. These patients may never see full recovery. Additionally, these patients are generally confined to the time and location of their physical therapy sessions for rehabilitation exercise. These existing devices generally do not allow weight to be placed on the compromised limb, nor do they facilitate the biomechanics of a normal gait motion in either the recently amputated limb or the remaining healthy limb that is necessary to avoid irreversible physiological consequences and avoid further medical intervention.

BRIEF SUMMARY

The following presents a simplified summary in order to provide a basic understanding of some aspects of the claimed subject matter. This summary is not an extensive overview. It is not intended to either identify key or critical elements or to delineate the scope of the claimed subject matter. Its sole purpose is to present some concepts in a simplified form as a prelude to the more detailed description that is presented later.

The described apparatuses and methods relate to medical devices and more particularly to medical walkers for those with unilaterally compromised mobility. While conventional walkers assist in stabilizing the patient while walking, they are not well-suited to amputee or monoplegic patients because they do not provide adequate support or muscle activation for the compromised limb. As a result, such patients may find it difficult or impossible to use a conventional walker for mobility. Other means for providing mobility to amputee patients either do not allow the compromised limb to be exercised though a natural walking motion, such as a wheelchair, or are prohibitively expensive, such an exoskeleton robot.

The medical walker described herein, in aspects, gives a patient mobility by providing a leg brace support for the compromised limb with a flexible connection to the walker that guides the compromised limb through a biomechanically proper walking motion, thus allowing the compromised limb to be exercised. In aspects, the described medical walker facilitates the biomechanics of a normal gait motion, including the muscle activations in the gait cycle. For an amputee patient or a patient with an otherwise compromised limb, embodiments of the walker allow the compromised limb to bear weight, activate muscles in the compromised limb, and allow the patient to walk a normal gait pattern with proper biomechanics. This prevents disease processes from accelerating, reduces pain, and strengthens the bones and muscles in the compromised limb. In addition, embodiments of the described walker can be portable, allowing the patient to practice walking outside of the time and location constraints of physical therapy sessions. The relatively streamlined design allows the walker to be used in a variety of settings, including but not limited to, physical therapy, hospitals, clinics, and the home. Further, the described walker can be used much earlier in the recovery period following surgery than a prosthetic limb can be fabricated or used. A return to walking as quickly as possible can benefit the patient's attitude toward recovery and physical therapy, as well as the strengthening muscles and bones of the patient.

In embodiments, a medical walker for use by a user with a compromised limb includes a wheeled frame adapted to move along a floor surface and support at least a portion of the user's weight; and a compromised limb gait system attached to the wheeled frame. The compromised limb gait system is configured to connect to the compromised limb of the user and guide the compromised limb through a simulated gait motion. The compromised limb gait system includes a yoke that connects a leg brace to a compromised limb gait system, where the brace is connected to the compromised limb of the user and at least one swing linkage, wherein the swing linkage permits movement in substantially a single plane and connects the yoke to the wheeled frame. The compromised limb gait system also includes a hard stop that limits the rearward motion of the swing linkage.

To the accomplishment of the foregoing and related ends, certain illustrative aspects of the claimed subject matter are described herein in connection with the following description and the annexed drawings. These aspects are indicative of various ways in which the subject matter may be practiced, all of which are intended to be within the scope of the claimed subject matter. Other advantages and novel features may become apparent from the following detailed description when considered in conjunction with the drawings.

BRIEF DESCRIPTION OF THE FIGURES

The apparatuses, devices, and methods may be better understood by referring to the following description in conjunction with the accompanying drawings, in which like numerals indicate like structural elements and features in various figures. The components in the figures are not necessarily to scale, and simply illustrate the principles of the apparatuses, devices and methods. The accompanying drawings illustrate only possible embodiments of the apparatuses, devices and methods and are therefore not to be considered limiting in scope.

DESCRIPTION

Figure 1:
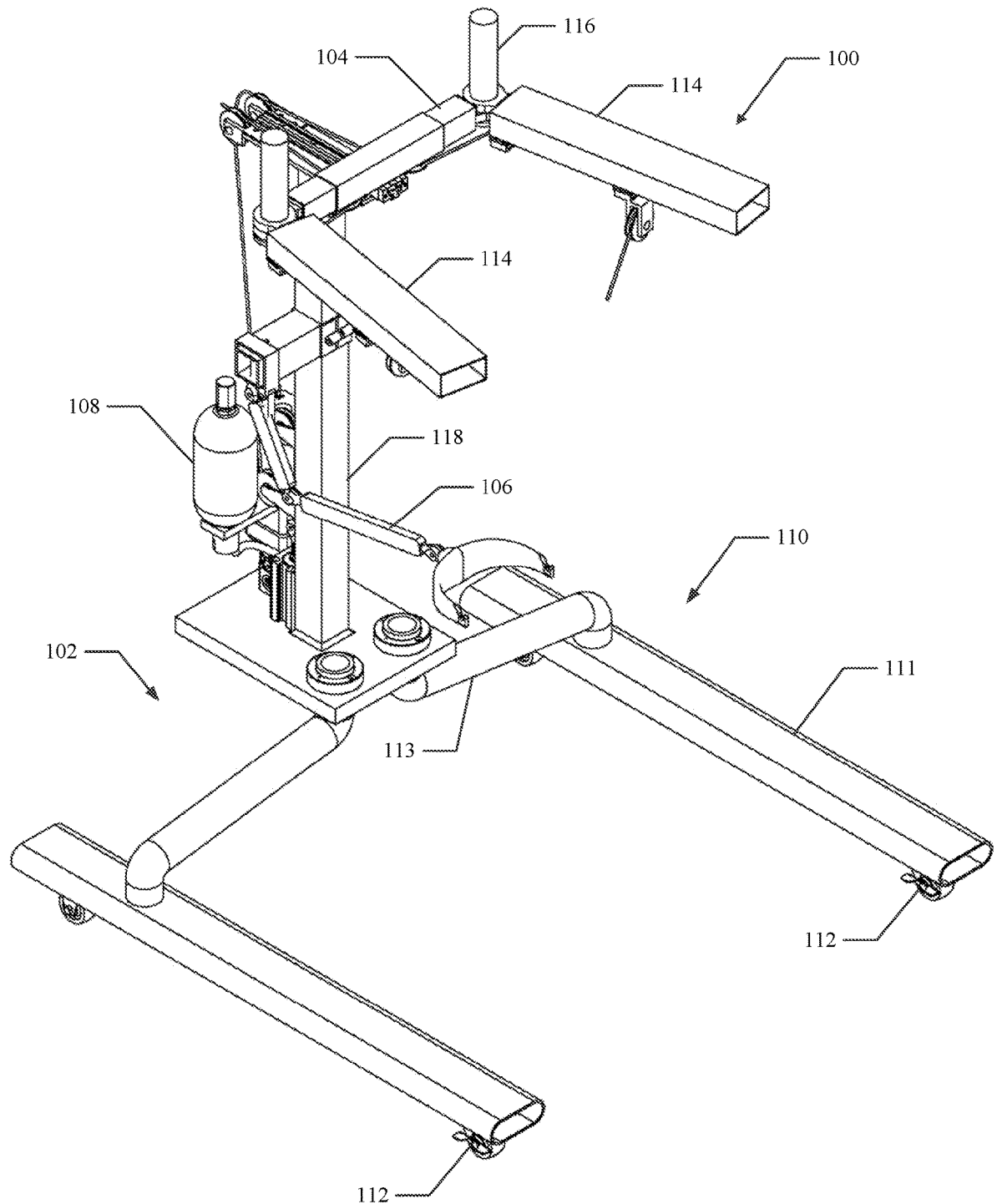
FIG. 1 is a perspective view of an embodiment of a medical walker.

Aspects of the system and methods are described below with reference to illustrative embodiments. The references to illustrative embodiments below are not made to limit the scope of the claimed subject matter. Instead, illustrative embodiments are used to aid in the description of various aspects of the device. The description, made by way of example and reference to illustrative reference is not meant to be limiting as regards any aspect of the claimed subject matter.

The described apparatuses relate to medical devices and more particularly to medical walkers for those with unilaterally compromised mobility. The terms "medical walker" and "walker" are used interchangeably herein. In aspects, the described medical walker facilitates the biomechanics of a normal gait motion, including the muscle activations in the gait cycle. For an amputee patient or a patient with an otherwise compromised limb, embodiments of the walker allow the compromised limb to bear weight, activate muscles in the compromised limb, and allow the patient to walk a normal gait pattern with proper biomechanics. This prevents disease processes from accelerating, reduces pain, and strengthens the bones and muscles in the compromised limb. In addition, embodiments of the described walker can be portable, allowing the patient to practice walking outside of the time and location constraints of physical therapy sessions. The relatively streamlined design allows the walker to be used in a variety of settings, including but not limited to, physical therapy, hospitals, clinics, and the home. Further, the described walker can be used much earlier in the recovery period following surgery than a prosthetic limb can be fabricated or used. A return to walking as quickly as possible can benefit the patient's attitude toward recovery and physical therapy, as well as the strengthening muscles and bones of the patient.

While conventional walkers assist in stabilizing the patient while walking and provide upper-body support, they are not well-suited to amputee or monoplegic patients because they do not provide adequate support or muscle activation for the compromised limb. Additionally, conventional walkers do not facilitate pelvic motion. Thus, users of conventional walkers are still vulnerable to physiological breakdowns. As a result of the short comings of conventional walkers, amputee or monoplegic patients may find it difficult or impossible to use a conventional walker for mobility. Other means for providing mobility to amputee patients either do not allow the compromised limb to be exercised though a natural walking motion, such as a wheelchair, or are prohibitively expensive, such an exoskeleton robot. The medical walker described herein, in aspects, gives an amputee patient mobility by providing a leg brace support for the compromised limb with a flexible connection to the walker that guides the compromised limb through a biomechanically proper walking motion, thus allowing the compromised limb to be exercised.

General Overview

Referring to FIGS. 1-5, in an embodiment, a medical walker 100 comprises a frame 102, an upper body support 104, a compromised limb gait system 106, and an unweighting system 108. The frame 102 provides the general support or structure for the medical walker 100 and can be implemented in a variety of ways. In general, it is formed from a lightweight, but durable material with sufficient strength to support most or all of the weight of a patient. The frame 102 is shaped to provide stability, while not interfering with movement of the patient's legs in a typical walking motion. In embodiments, the frame 102 includes a base 110 supported by a set of wheels 112 that allow the walker 100 to move with the patient as they walk.

In embodiments, the upper body support 104 is attached to the frame 102 and allows a patient to place or rest at least a portion of their upper body on the upper body support 104, thereby reducing the amount of weight placed on the compromised limb. In aspects, the upper body support 104 can facilitate a patient's upright posture or position, beneficial to achieving a proper gait motion. It can provide the patient with an easy grip to steer or direct the walker 100. In the illustrated embodiment, the upper body support 104 includes a forearm rest 114 and hand grips 116. In an alternate embodiment, the upper body support 104 is an abdominal support 1900, shown and described in greater detail below.

In embodiments, the unweighting system 108 reduces the amount of the patient's body weight that is placed on the patient's lower limbs. The unweighting system 108 can assist patients in regaining mobility as soon as possible by reducing the physical demands on their limbs while walking or standing. In an embodiment, the unweighting system 108 is adjustable with respect to the size of the patient and the amount of weight supported, allowing the weight supported by the patient's lower limbs to be gradually increased as the patient's strength increases. In an aspect, the unweighting system 108 includes a harness attached to and suspended from the frame 102 of the walker 100, shown and described in further detail in FIGS. 10-18 below. The patient can be seated in the harness or the harness can be attached to the patient to provide support.

Figure 6:
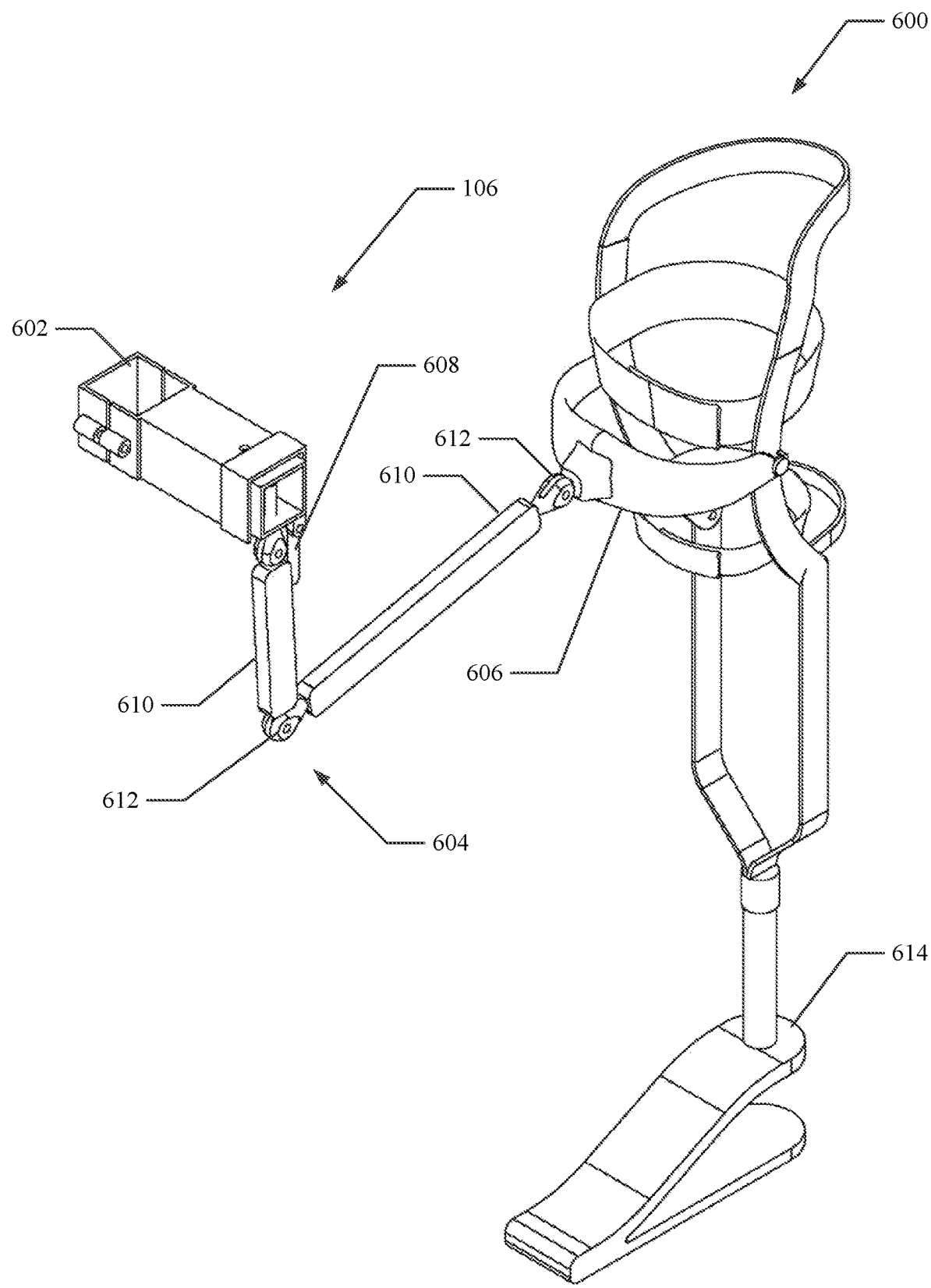
FIG. 6 is a perspective view of embodiments of a compromised limb gait system and a connected brace.
Figure 7:
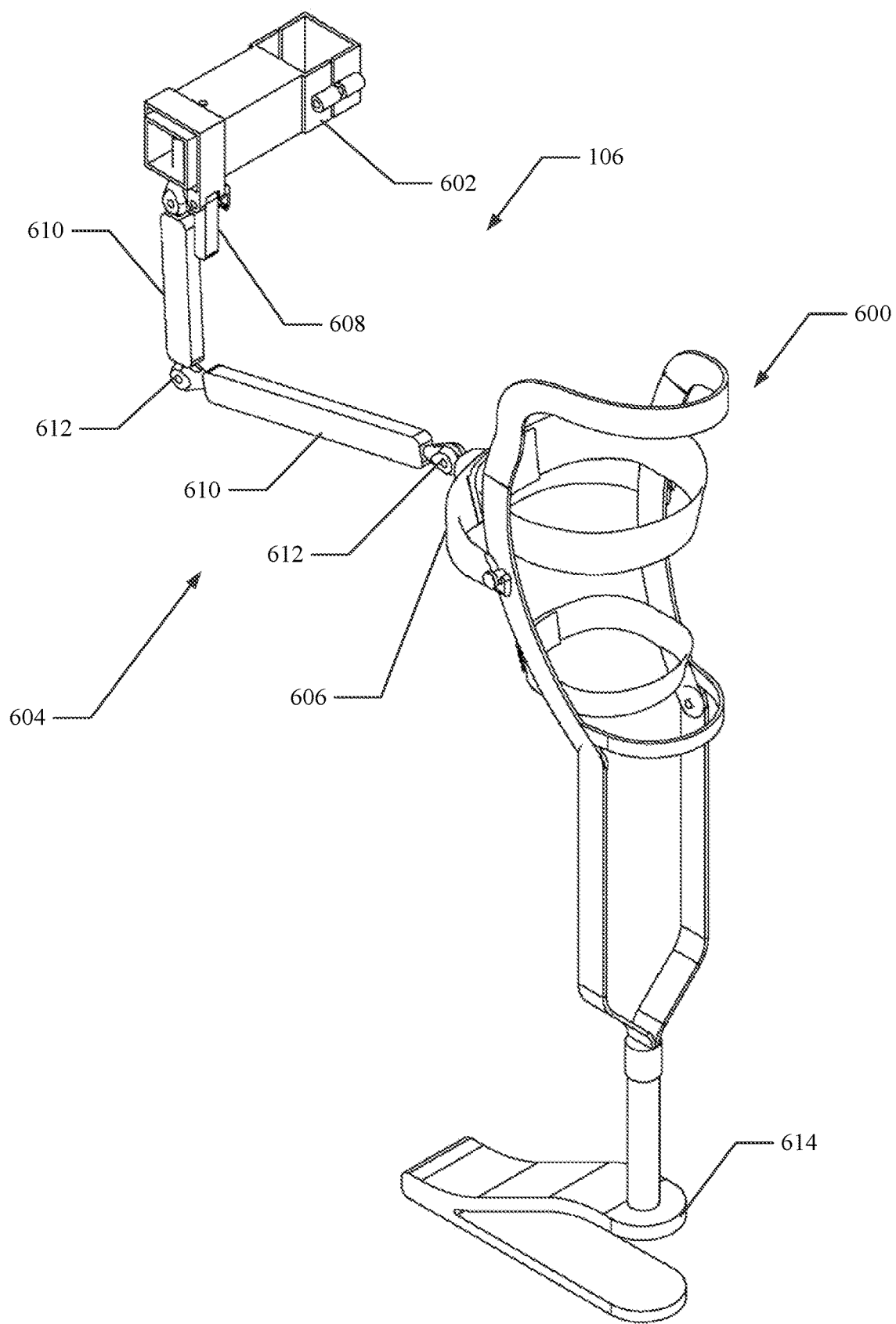
FIG. 7 is an alternate perspective view of the compromised limb gait system and brace of FIG. 6.
Figure 8:
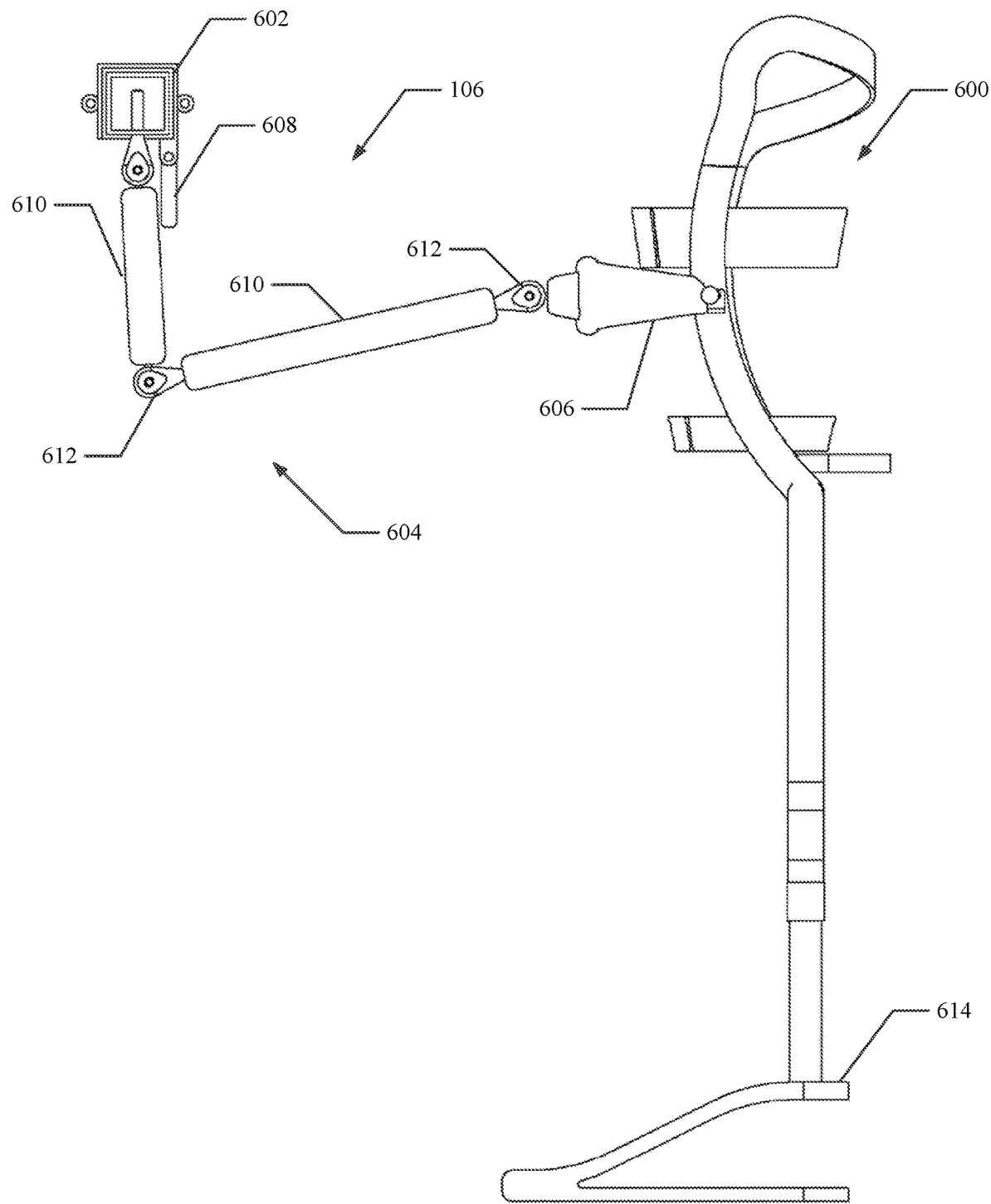
FIG. 8 is a left side view of the compromised limb gait system and brace of FIG. 6.

In embodiments, the compromised limb gait system 106 guides the patient's compromised limb though a simulated walking motion. A customizable leg brace 600, described below and shown in FIGS. 6-8, is fitted to the patient's compromised limb. The customizable leg brace 600 is then attached to the walker 100 through the compromised limb gait system 106. The compromised limb gait system 106 can restrict or direct motion of the compromised limb to encourage movement of the limb in the proper, biomechanical gait. In embodiments, the compromised limb gait system 106 can provide at least partial support for the attached leg brace 600, such that the frame 102 absorbs a portion of the weight of the patient. In addition, as described in more detail below, the leg brace 600 can provide support for the compromised limb and the patient. The walker 100 encourages the patient to shift some of their weight onto the compromised limb, gradually strengthening the limb, activating those muscles and facilitating mobility and rehabilitation. By unweighting the patient and/or encouraging proper gait motion, the illustrated walker can improve patient mobility more quickly than conventional walkers.

Frame

Referring once again to FIGS. 1-5, the frame 102 provides the general support or structure for the medical walker 100. Naturally, this frame 102 can be implemented in a variety of ways to support the elements of the walker 100. In embodiments, the frame 102 comprises a wheeled base 110 and a support structure 118 extending vertically from the base 110. The frame can be made of a material such as aluminum or steel such that the frame is sufficiently strong to support the weight of the walker as well as the weight of the patient. In depicted embodiments, the base 110 consists of two generally horizontal bars 111 substantially parallel to the direction of motion of the patient when the patient is walking straight ahead. The horizontal bars 111 are on the left and right sides of the walker 100, and when in use, the patient is positioned between the horizontal bars 111. The base 110 is configured to allow the patient to take normal steps or strides without bumping or impacting the base 110. As shown, a connecting bar or bars 113 located at or near the front of the base 110 connects the horizontal bars 111. The connecting bar 113 is positioned such that it will not interfere with a normal stride of a patient. It is understood that the base 110 can be implemented with any configuration that is stable and avoids interference with the stride of the patient.

A plurality of wheels 112 extends from the bottom of the horizontal bars 1906. In the depicted embodiment, a wheel 112 is positioned at the anterior and posterior end of each horizontal bar 111, for a total of four wheels 112. The base 110 and wheels 112 enhance the stability of the walker 100, and reduce the likelihood that the walker 100 can tip over during use, further injuring the patient. The wheels 112 also allow the walker 100 to move smoothly with the patient as they walk. In embodiments, one or more of the wheels 112 can include a braking mechanism that allows the patient to fix the position of the walker 100. The patient can elect to engage the braking mechanism to hold the walker 100 in place when entering into the walker 100, or when exiting it.

Figure 2:
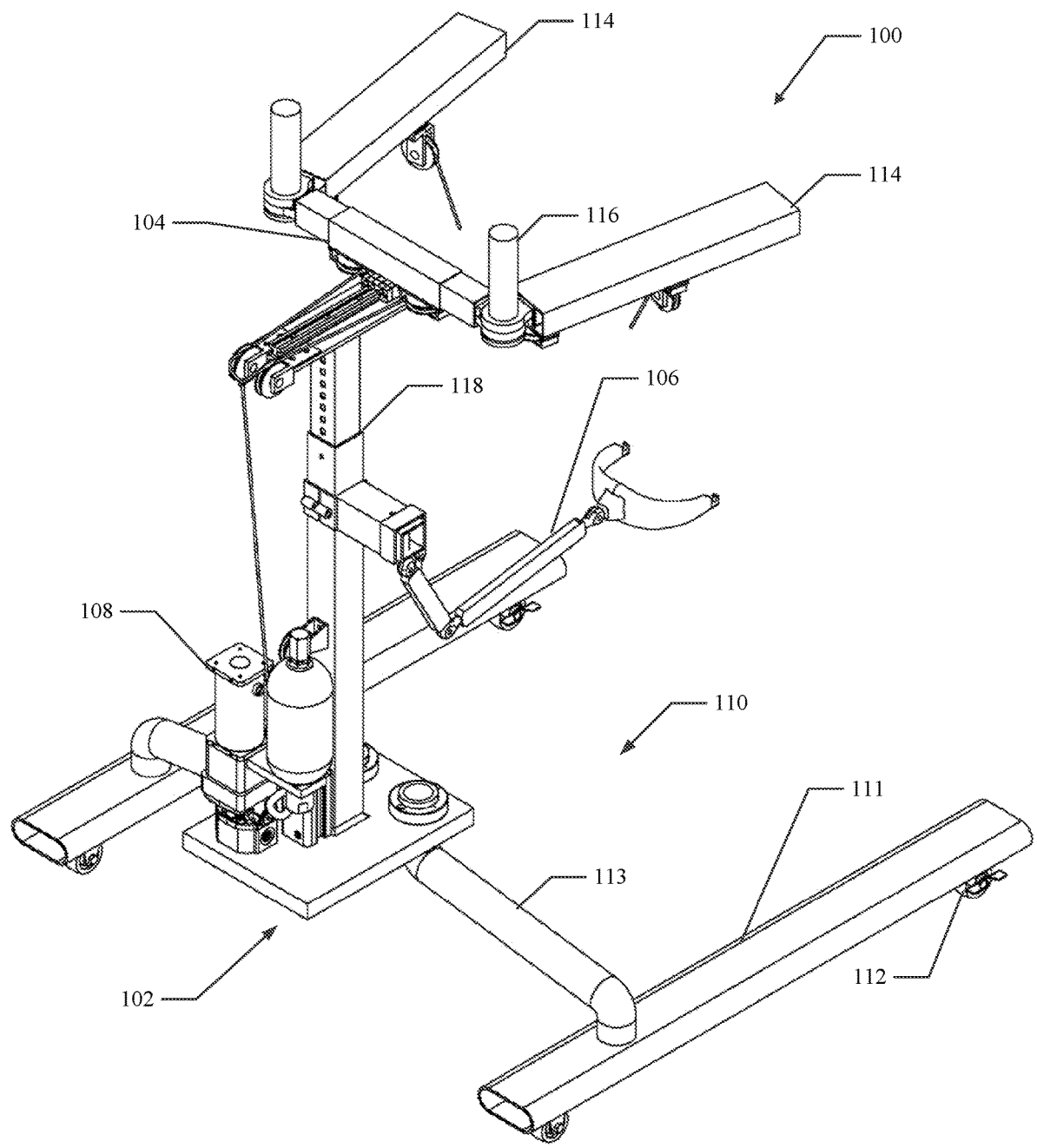
FIG. 2 is an alternate perspective view of the medical walker of FIG. 1.
Figure 3:
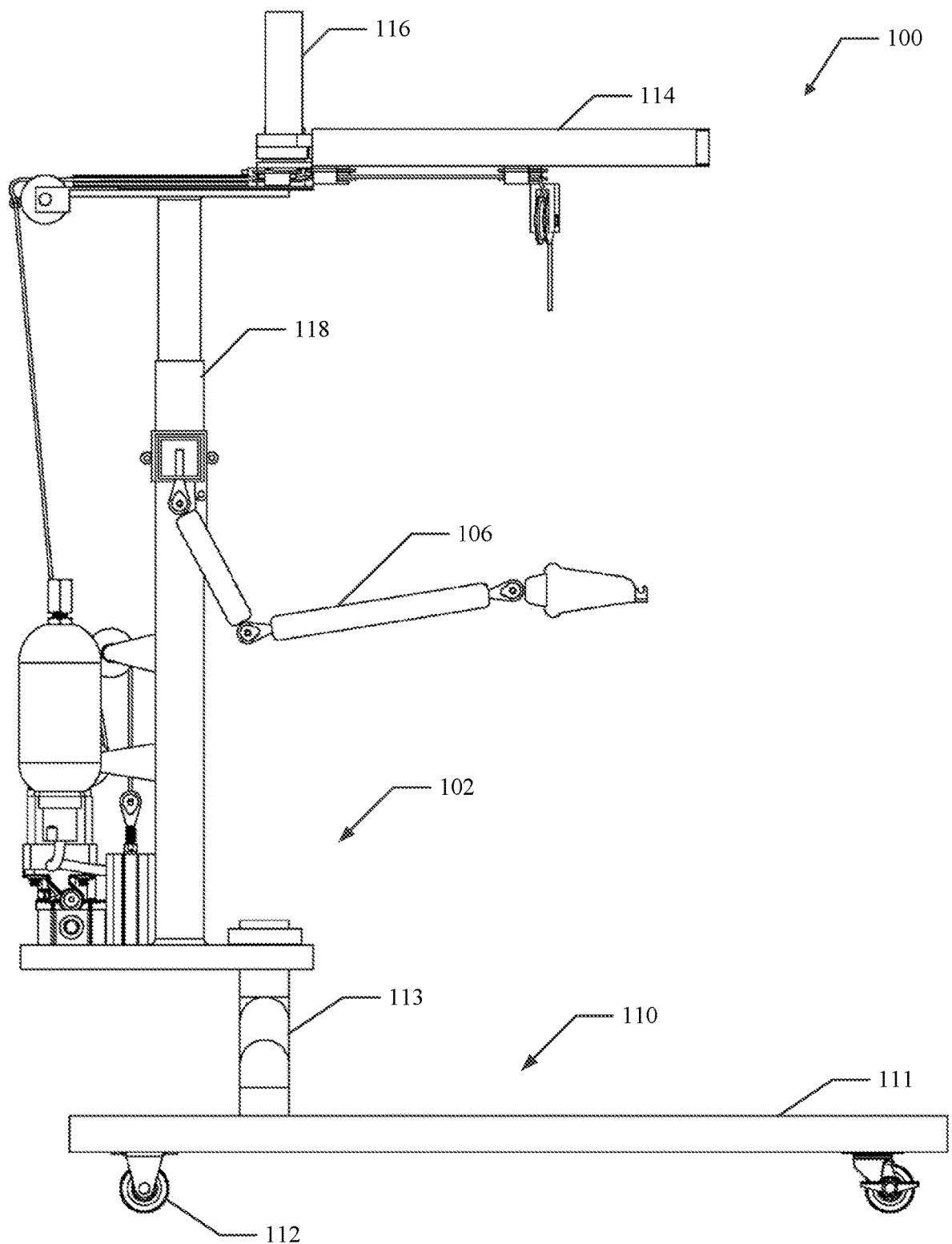
FIG. 3 is a left side view of the medical walker of FIG. 1.
Figure 4:
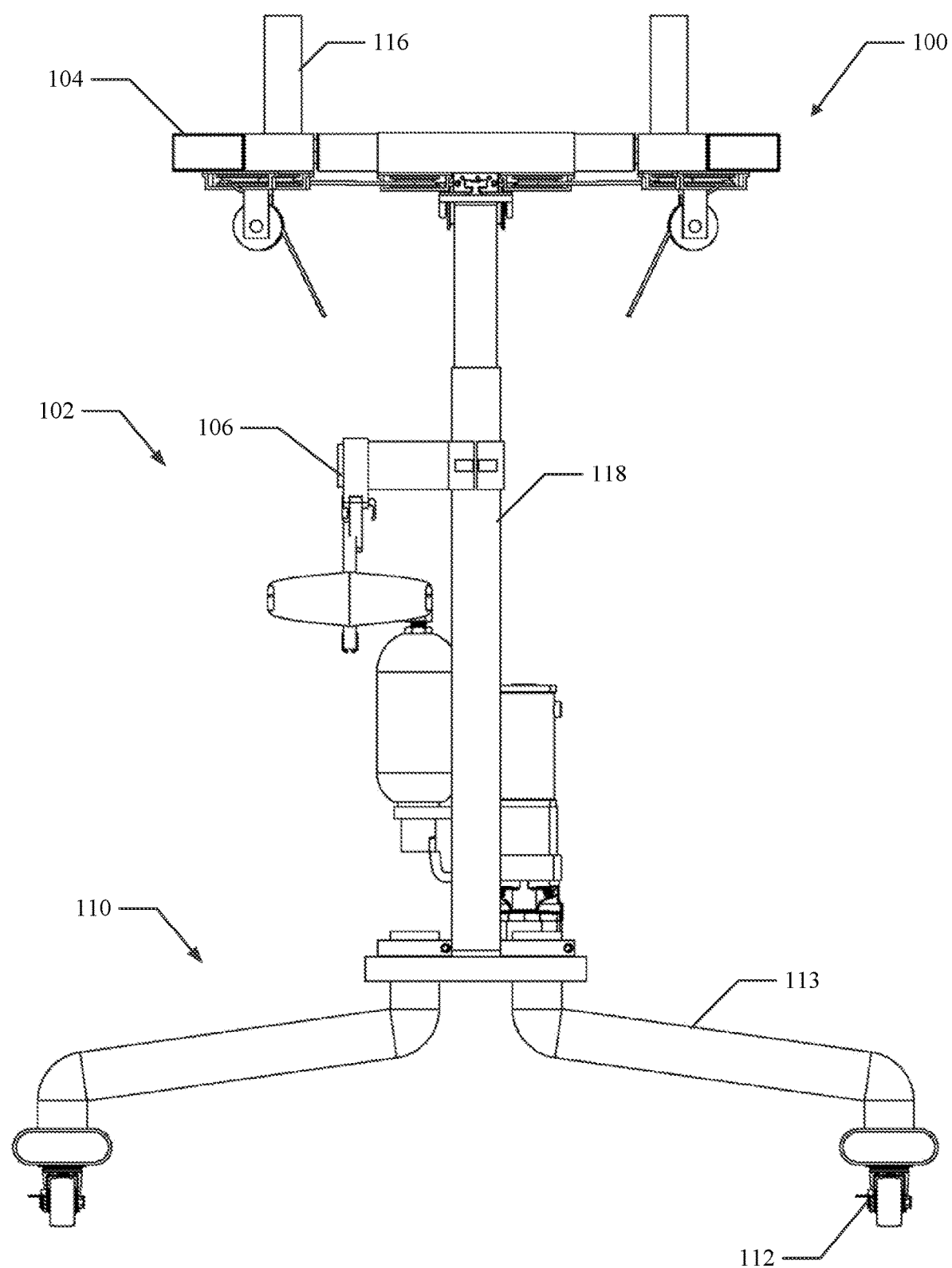
FIG. 4 is a front view of the medical walker of FIG. 1.
Figure 5:
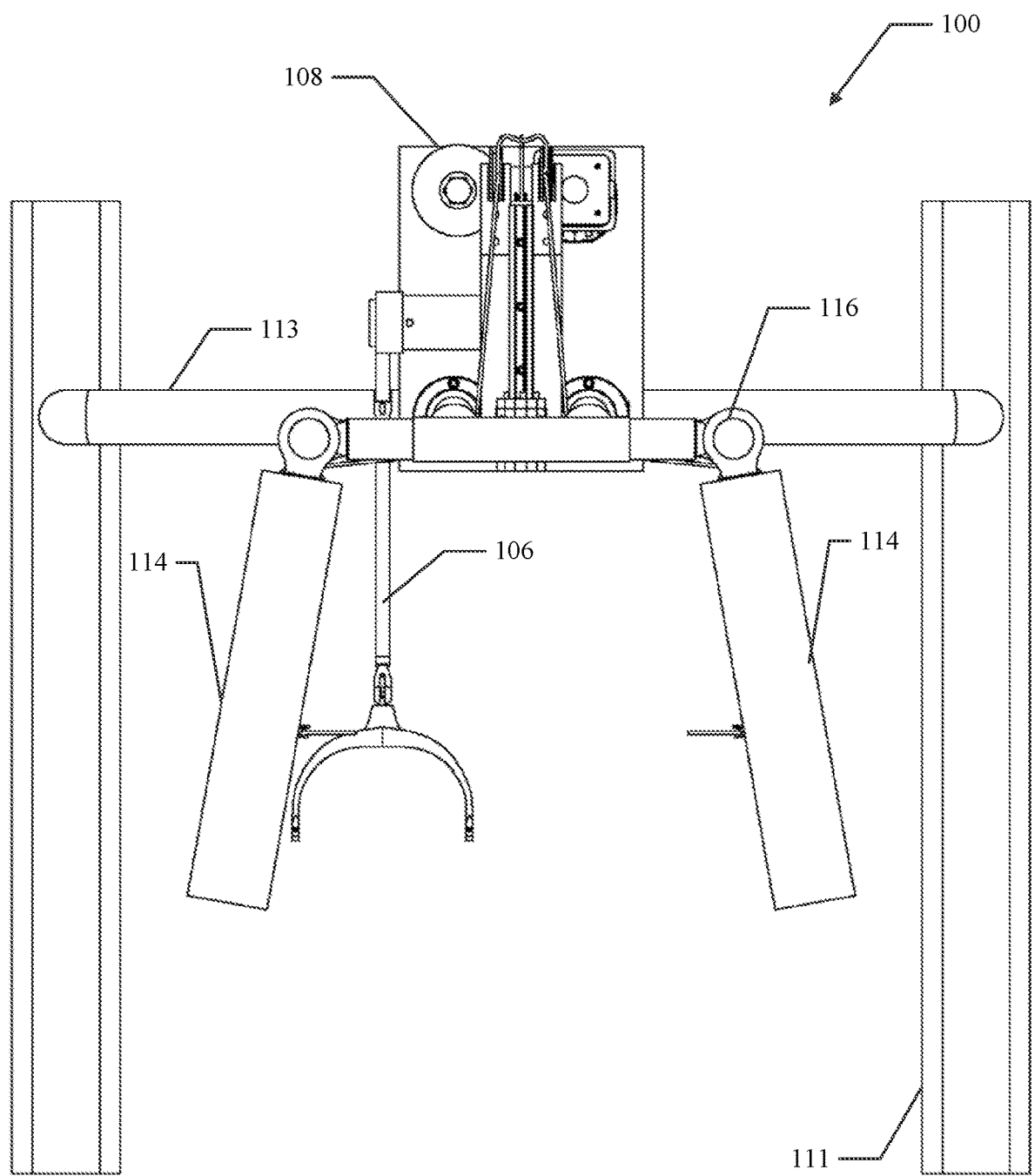
FIG. 5 is a top view of the medical walker of FIG. 1.

In the embodiments depicted in FIGS. 1-5 and 9-18, the frame 102 includes a support structure 118 shown as a stanchion extending upwards from the wheeled base 110 and connecting to the upper body support 104. In an embodiment, the support structure 118 can be adjusted to lengthen or shorten to accommodate users of differing heights. For example, the support structure 118 can be implemented using telescopic rods, which can be fixed in position by tightening the perimeter of the external rod around an inner rod. In other embodiments, the telescopic rods can include a series of apertures such that the length of the support structure 118 can be fixed by aligning apertures in the external rod and internal rod and inserting a pin into the aperture, as can be seen in FIG. 2. In an embodiment, if the upper body support 104 includes a forearm rest 114, the support structure 118 can be adjusted so that the attached forearm rest 114 is at approximately the patient's shoulder height. In an embodiment, if the upper body support 104 is an abdominal support 1900, shown and described with respect to FIGS. 19-23, the support structure 118 can be adjusted so that the attached abdominal support 1900 is at approximately the height of the patient's abdomen. The support structure 118 can be strong enough to support the weight of the upper body support 104 as well as the weight of the patient. In an embodiment, the unweighting system 108 can be connected to a portion of the support structure 118 such that the support structure 118 bears the portion of the patient's weight supported by the unweighting system 108. Thus, the support structure 118 therefore is, in one aspect, sufficiently sturdy to support the weight of the patient and the upper body support 104 attached to the support structure 118. In other embodiments, configuration of the elements making up the support structure 118 may differ, while still allowing for the unweighting system 108 to be mounted at pelvic height and the upper body support 104 at the appropriate height to support the patient's upper body.

In the embodiment depicted in FIGS. 1-5, the upper body support 104 includes a forearm rest 114. The illustrated forearm rest 114 is a generally flat surface comprising a left armrest, a right armrest, and a center, connecting portion. The left armrest and right armrest extend from the center portion at an angle, such that when in use, the patient's left and right forearm may comfortably rest on the left and right armrests, respectively. Two handles or handgrips 116 extend vertically from the center portion of the forearm rest 114, which allow the patient to grip the walker 100. The handgrips 116 may be any shape that allows the patient to grip the walker 100 comfortably, for example, the two vertical cylinders shown. The underside of the center portion of the forearm rest 114 is attached to the support structure 118—in this embodiment, a stanchion. Thus, by adjusting the height of the support structure 118, the height of the forearm rest 114 may be adjusted to ensure that when the walker 100 is in use, the patient's shoulders and pelvis are at the proper height for a natural gait motion and that the patient is in an erect, upright posture.

The forearm rest 114 can provide greater support than the bars of a conventional walker. By supporting a patient's forearms, the patient utilizes muscles in the shoulder and bicep to support their body weight instead of utilizing the muscles in the forearm and wrist, as in the case of a conventional walker. A walker 100 with a forearm rest 114 allows a patient to use a walker 100 earlier in the recovery process and when the patient would otherwise be unable to use a conventional walker due to the utilization of the larger muscle groups in the shoulder and bicep. In embodiments, the surface of the forearm rest 114 is cushioned to reduce the chance of the patient developing pressure sores and reduces the amount of weight on the patient's shoulders.

In the embodiment depicted in FIGS. 19-23, the walker 100 includes an abdominal support 1900 as an upper body support 104 in addition to or in place of a forearm rest 114. The abdominal support 1900 is shaped to receive and support the patient's abdomen while the patient is using the walker 100. The abdominal support 1900 curves such that it can snugly hold the patient's sides, and has an opening in the rear which allows the patient to enter the abdominal support 1900. The abdominal support 1900 is capable of supporting more weight than a conventional walker. When in use, the abdominal support 1900 encourages the patient to stand and walk with a natural, upright posture while allowing the patient's arms to swing freely.

Compromised Limb Gait System

Referring now to FIGS. 6-8, an embodiment of the compromised limb gait system 106 is shown with an attached leg brace 600. In the illustrated embodiment, the compromised limb gait system 106 includes a connector 602 that attaches the compromised limb gait system 106 to the frame 102, at least one swing linkage 604, a yoke 606, and a hard stop 608. As shown, the connector 602 can be implemented as a clamp that slides vertically with respect to the support structure 118 and can be fixed at a desired position. This permits the height of the compromised limb gait system 106 to be raised or lowered relative to the support structure 118 and customized for the height of the patient. In other embodiments, any suitable connector 602 can be used to attach the compromised limb gait system 106 to the frame 102 either at an adjustable or fixed height. The illustrated connector 602 provides an offset from the support structure 118. Where the support structure 118 is generally centered in the frame 102 the offset aligns the compromised limb gait system 106 with the compromised limb. While the illustrated embodiments are shown with a leg brace 600 for a compromised left leg, the connector 602 and compromised limb gait system 106 can be reoriented to connect to and support a leg brace 600 and compromised right leg.

The swing linkage 604 permits movement of the brace 600 and compromised limb in a single plane and connects the yoke 606 to the wheeled frame 102. In the illustrated embodiment, the swing linkage 604 includes one or more arms 610 connected via one or more hinge joints 612. The hinge joints 612 permit substantially planar movement of the arms 610, but restrict lateral movement. The yoke 606 connects the brace 600 to a compromised limb gait system 106. Frequently, patients with compromised limbs adapt their stride to make up for the weakness in the compromised limb. But this change in gait mechanics can injure or stress other muscles or joints. The compromised limb gait system 106 directs the brace 600 and compromised limb in the typical, generally longitudinal progress of the limb during walking. The swing linkages 604 and yoke 606 move with both the rotational and longitudinal movement of the limb, but restrict lateral movement, approximating the natural gait of the limb.

As shown, the yoke 606 connects to each side of the leg brace 600 with a pin joint or revolute joint. This allows the leg brace 600 to rotate freely with respect to the yoke 606, and restricts lateral movement. In embodiments, the leg brace 600 is detachable so that it can be fitted to the compromised limb of the patient. Once the leg brace 600 is fitted to the limb, the brace 600 can be attached to the compromised limb gait system 106 via the pin joints and moves in a natural manner. The yoke 606 and swing linkages 604 control movement of the brace 600 and compromised limb facilitating normal gait mechanics and encouraging proper walking motion.

The hard stop 608 on the swing linkage 604 limits the rearward motion of the swing linkage 604, which prevents the swing linkage 604 from extending too far to the rear of the walker 100. This encourages the patient to stride with the compromised limb, and discourages dragging of the limb. As shown in FIGS. 6-8, the hard stop 608 can be implemented as a simple bar that limits the rotation of the hinge joint 612, thereby limiting the movement of the arms 610. By stopping the rearward motion of the swing linkage 604, the hard stop 608 communicates to the patient when the simulated gait motion has been completed for a particular step and when it is time to begin another step and continue the simulate gait motion.

Figure 9A:
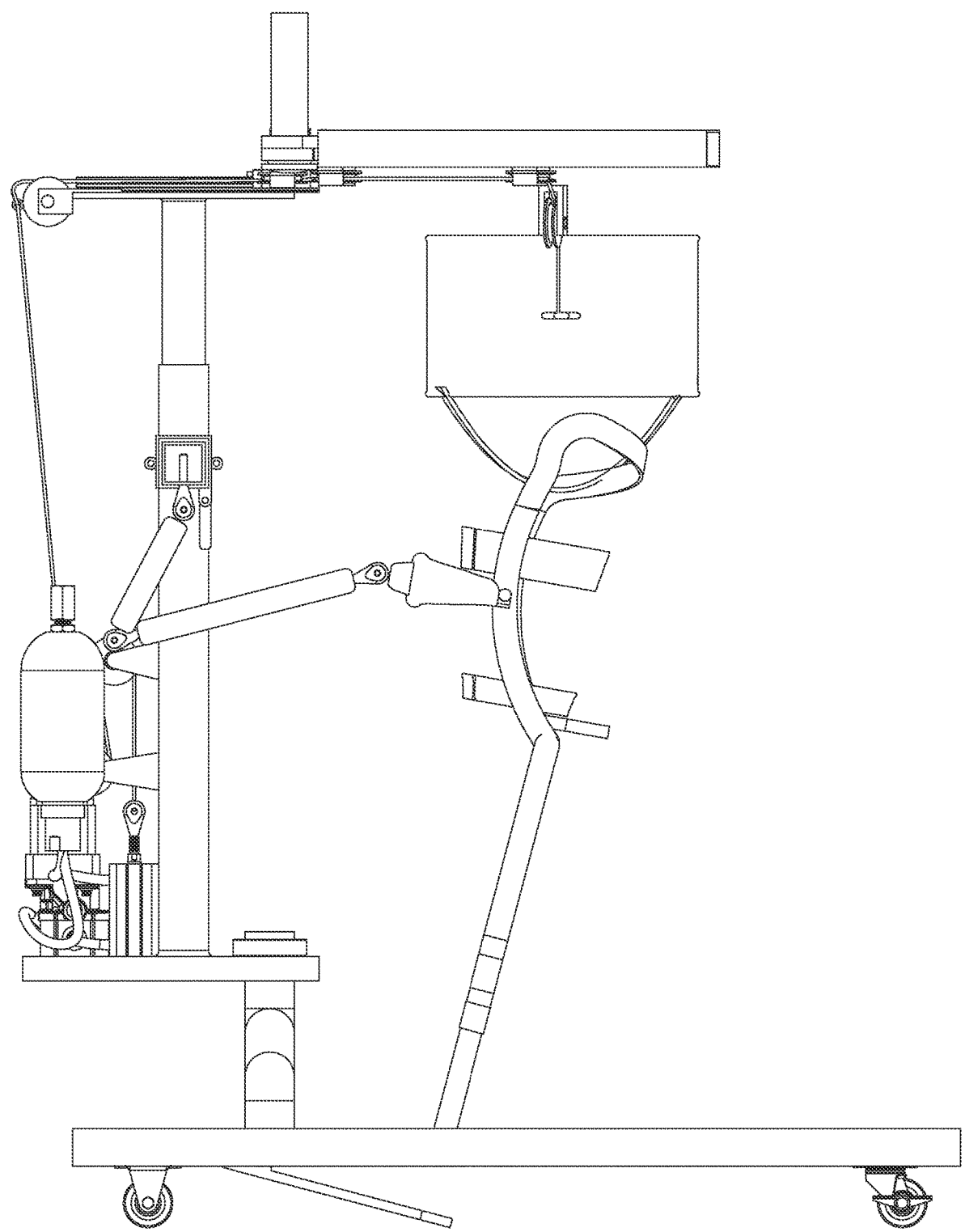
FIG. 9A is a left side view of an embodiment of the medical walker, where the brace is in a heel strike position.
Figure 9B:
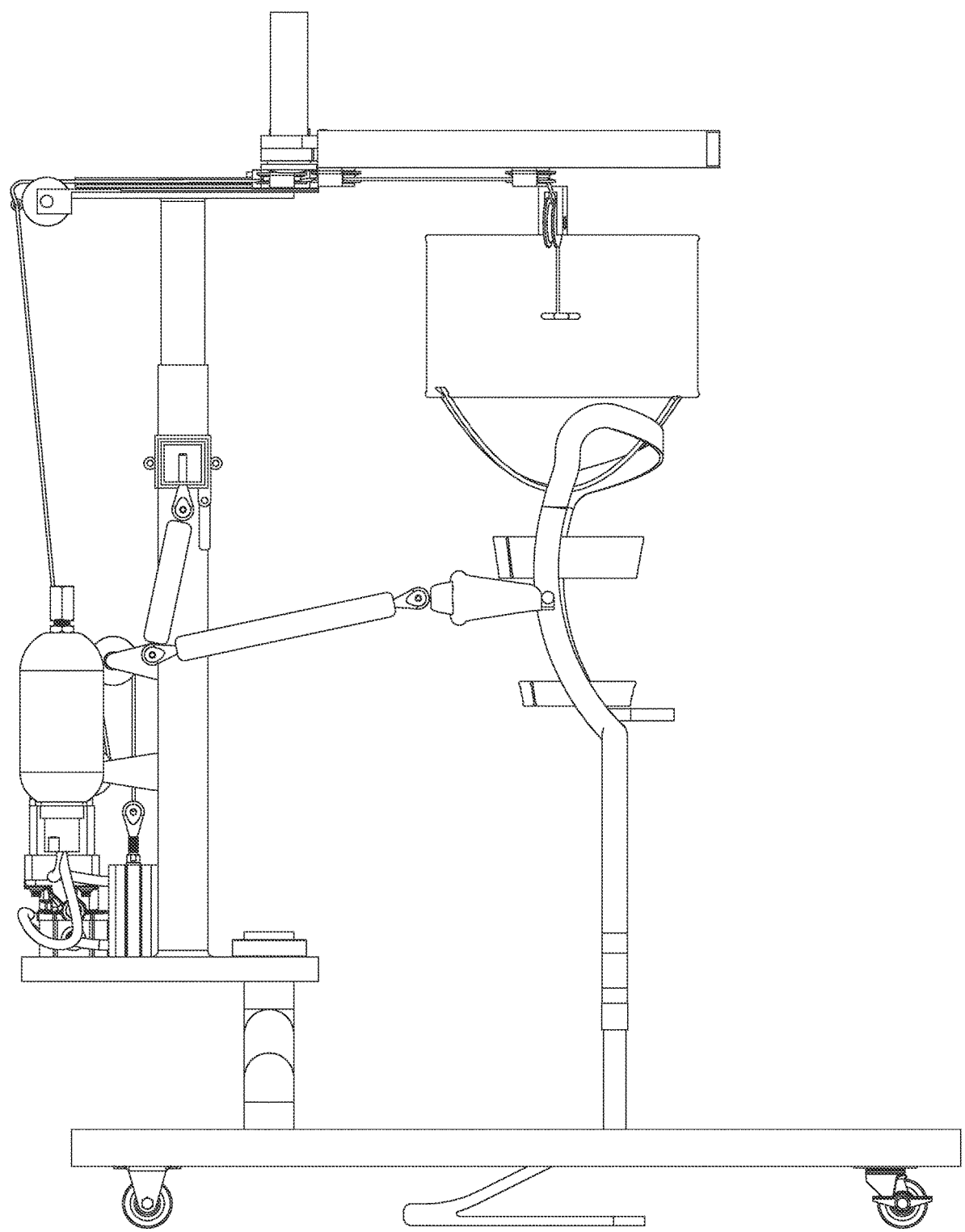
FIG. 9B is a left side view of an embodiment of the medical walker, where the brace is in a mid-stride position.
Figure 9C:
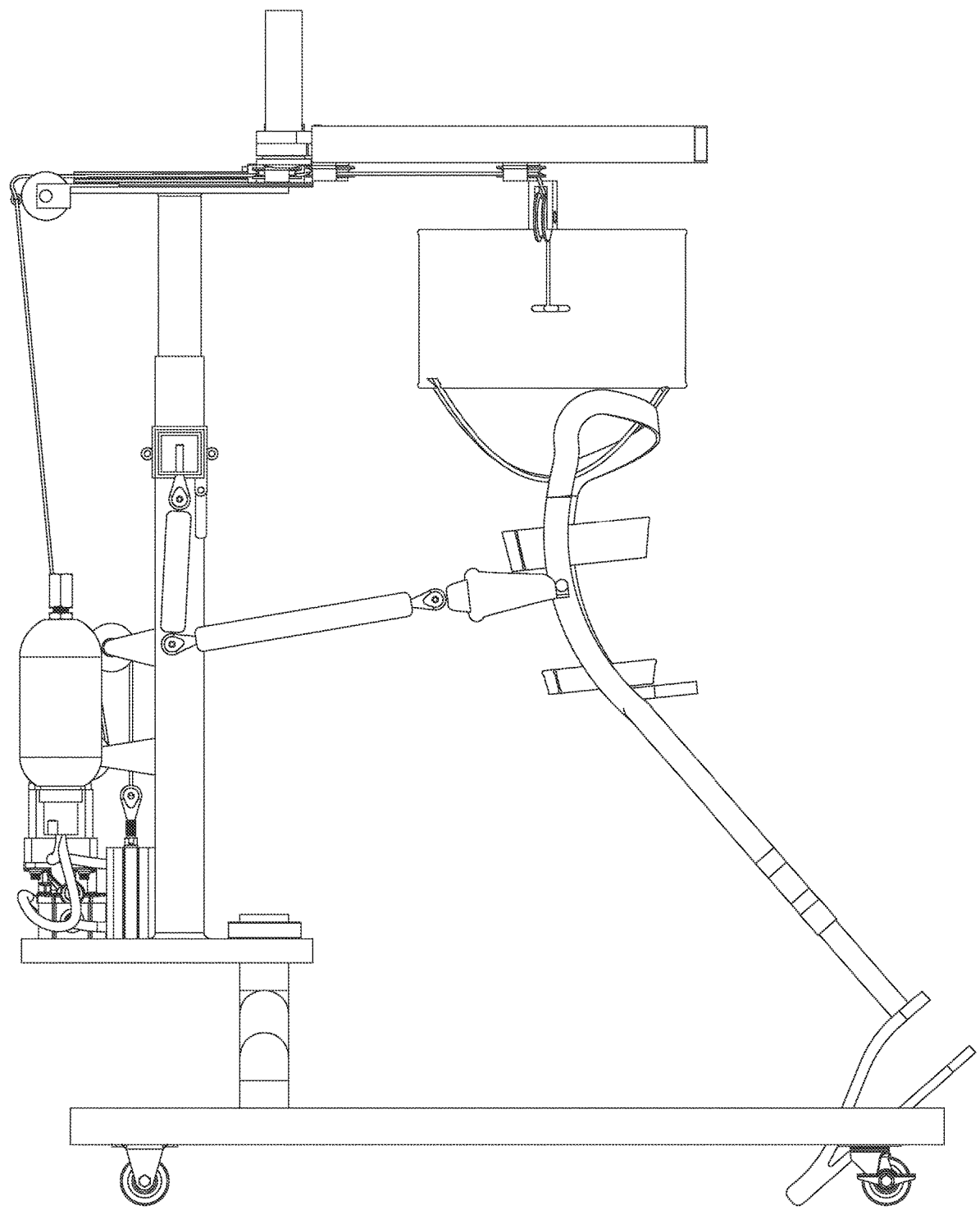
FIG. 9C is a left side view of an embodiment of the medical walker, where the brace is in a toe off position.
Figure 10:
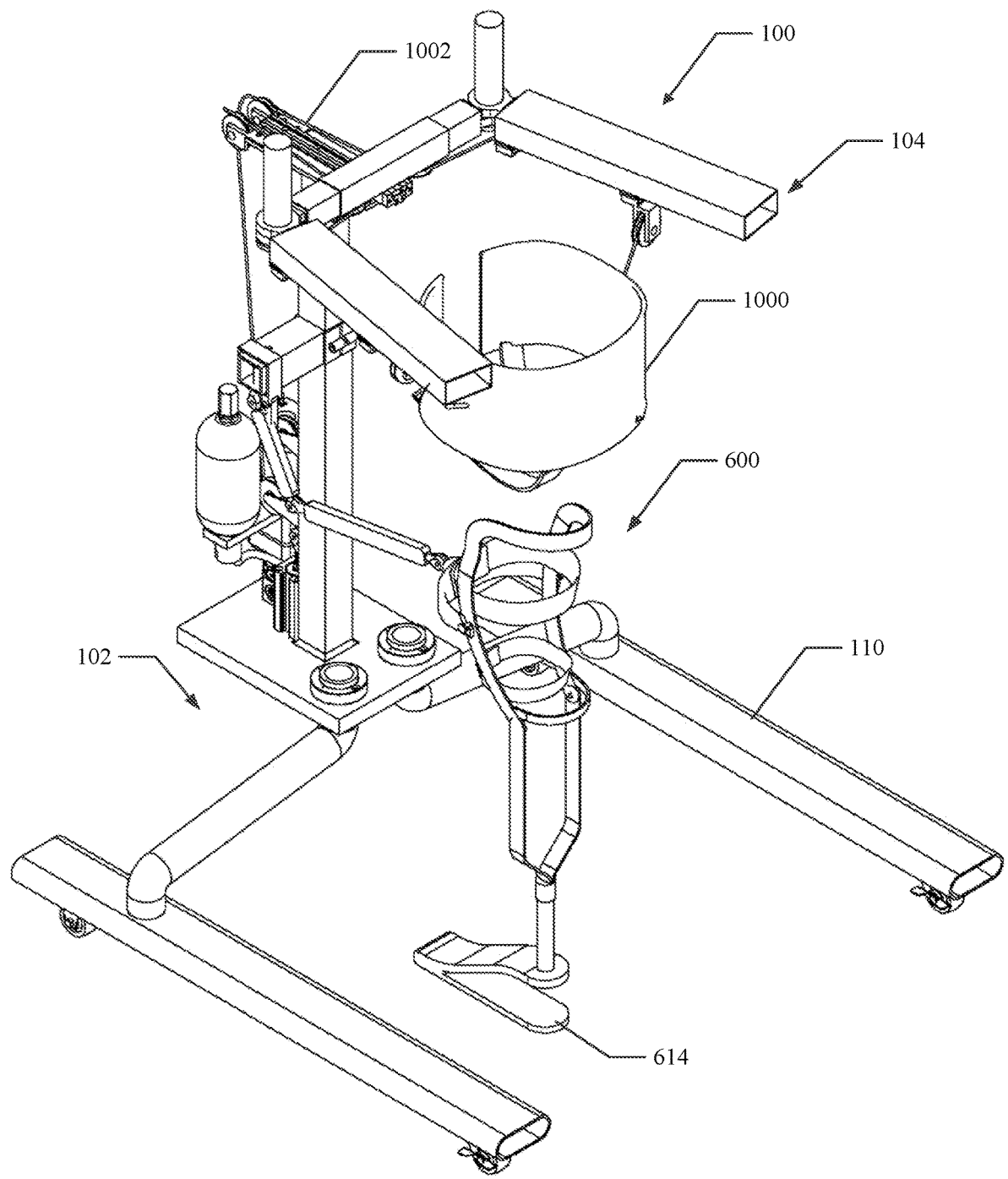
FIG. 10 is a perspective view of embodiments of the medical walker connected to a brace and an unweighting harness.
Figure 11:
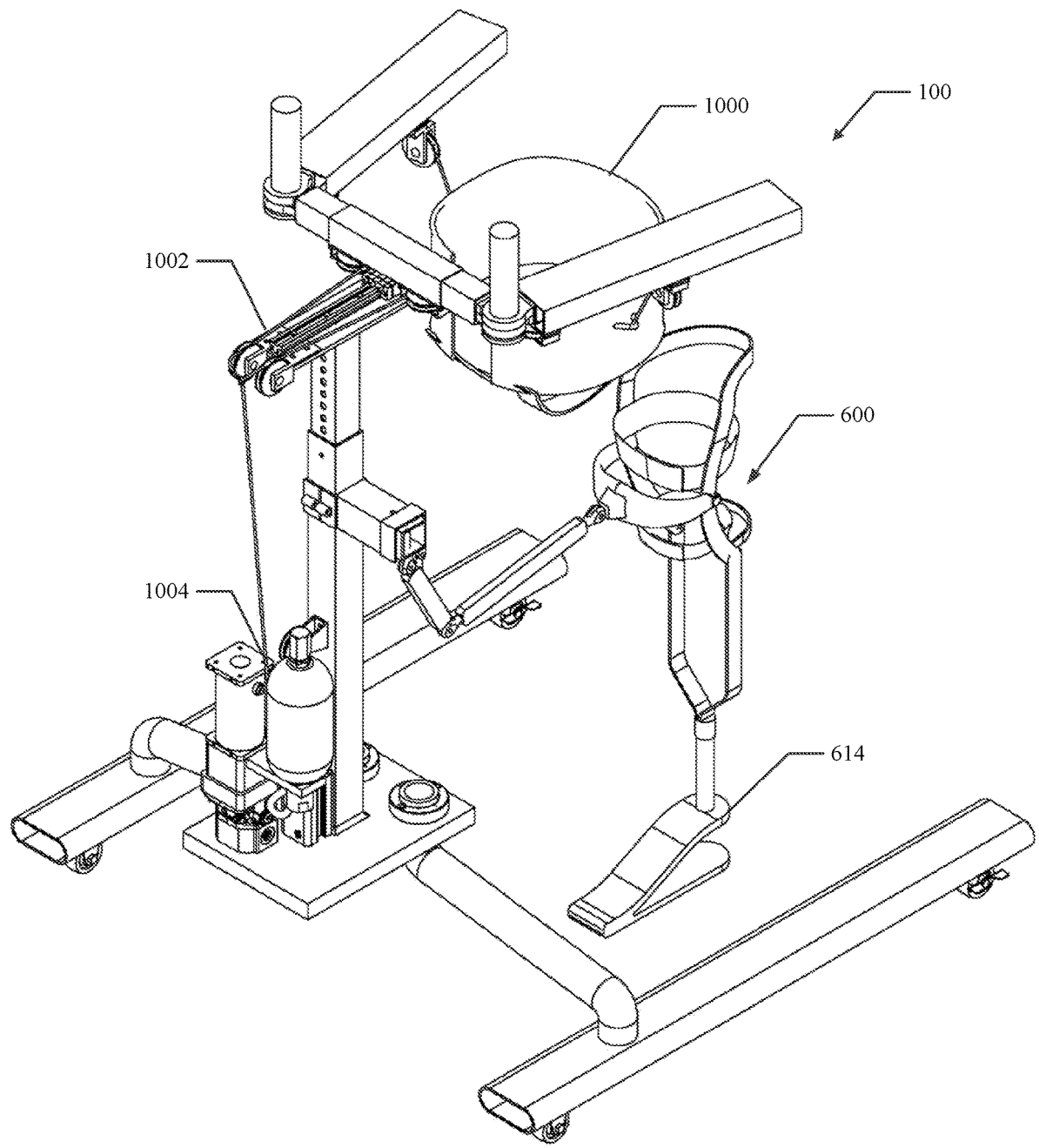
FIG. 11 is an alternate perspective view of the medical walker, brace, and unweighting harness of FIG. 10.
Figure 12:
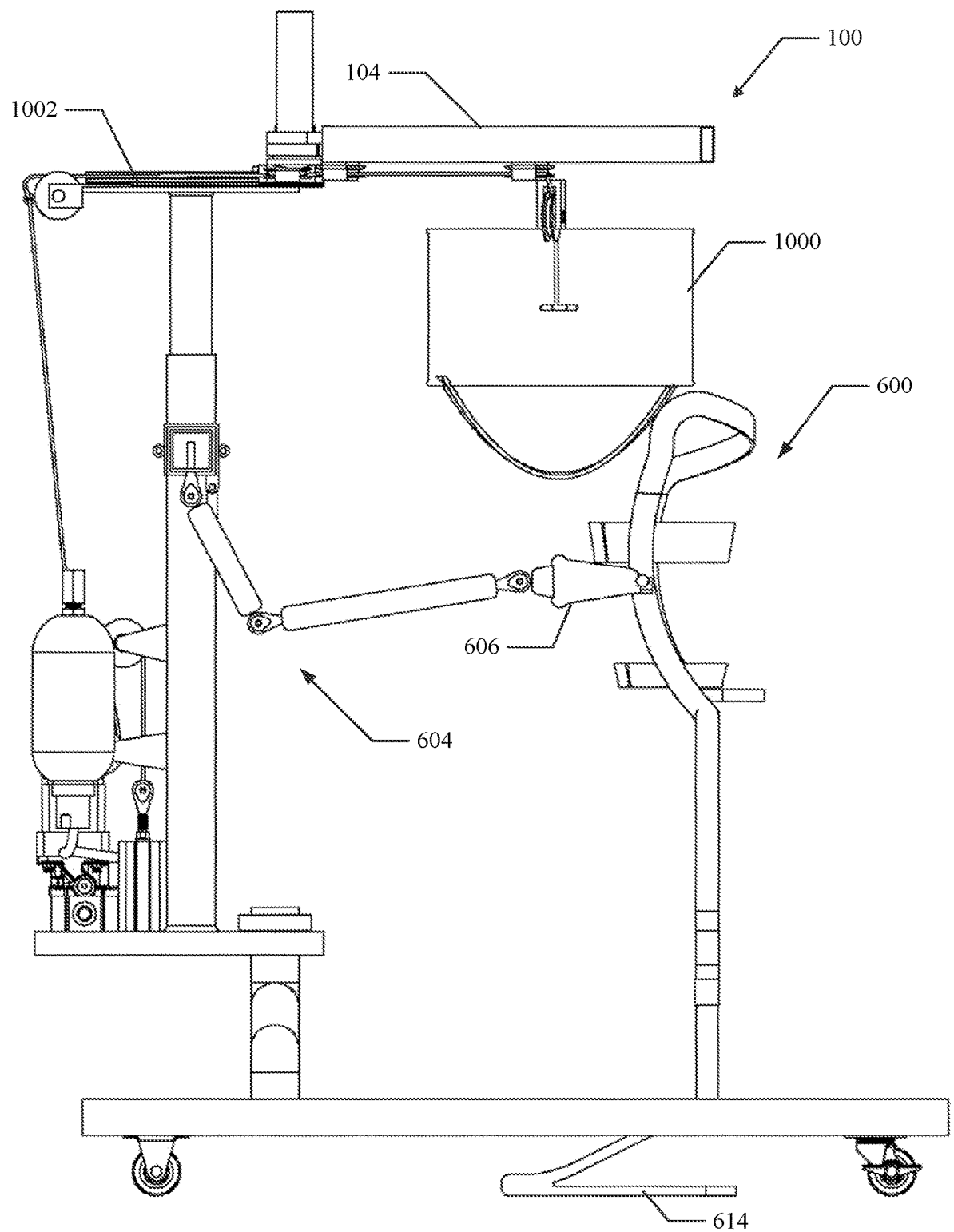
FIG. 12 is a left side view of the medical walker, brace, and unweighting harness of FIG. 10.
Figure 13:
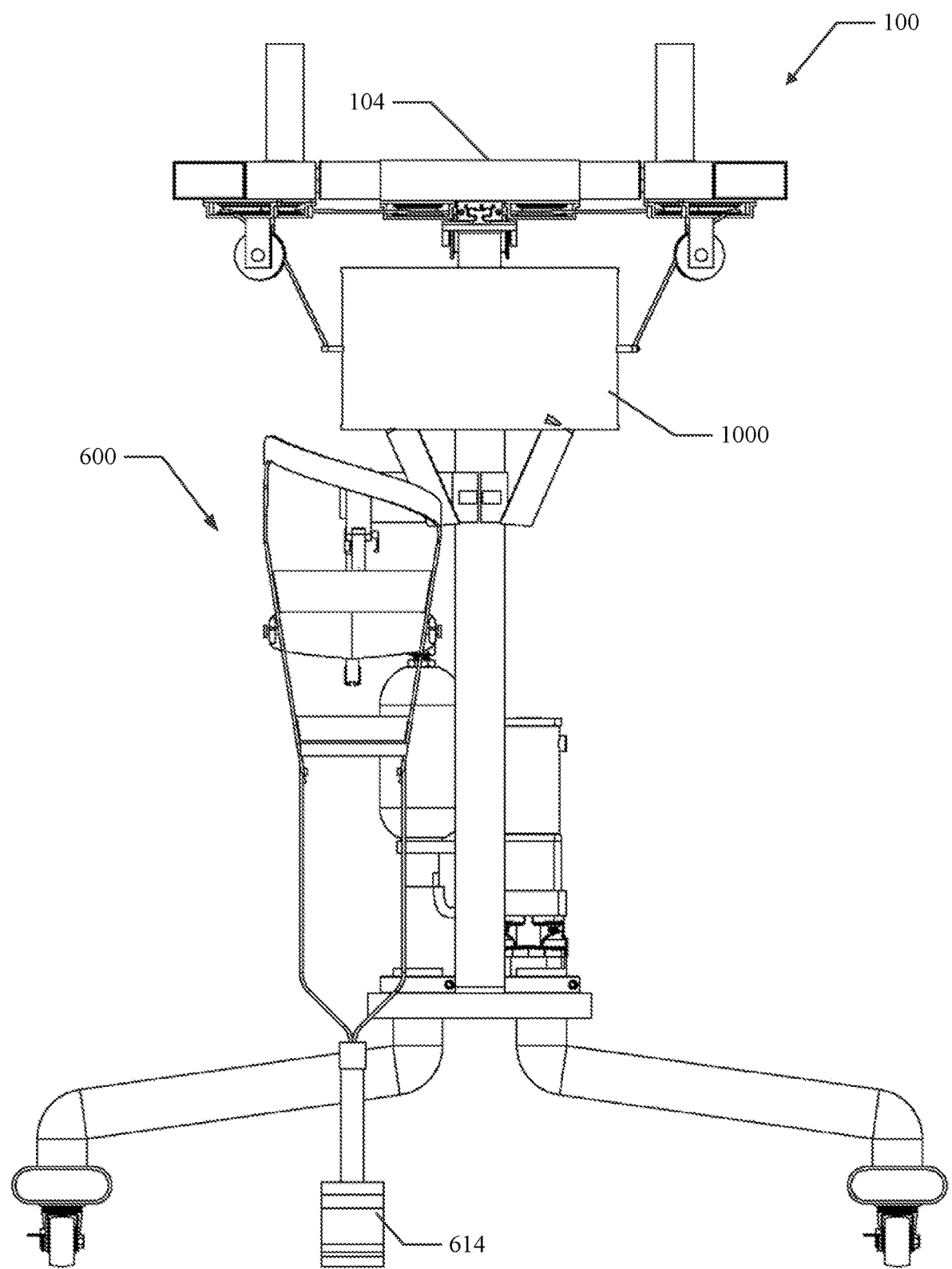
FIG. 13 is a rear view of the medical walker, brace, and unweighting harness of FIG. 10.
Figure 14:
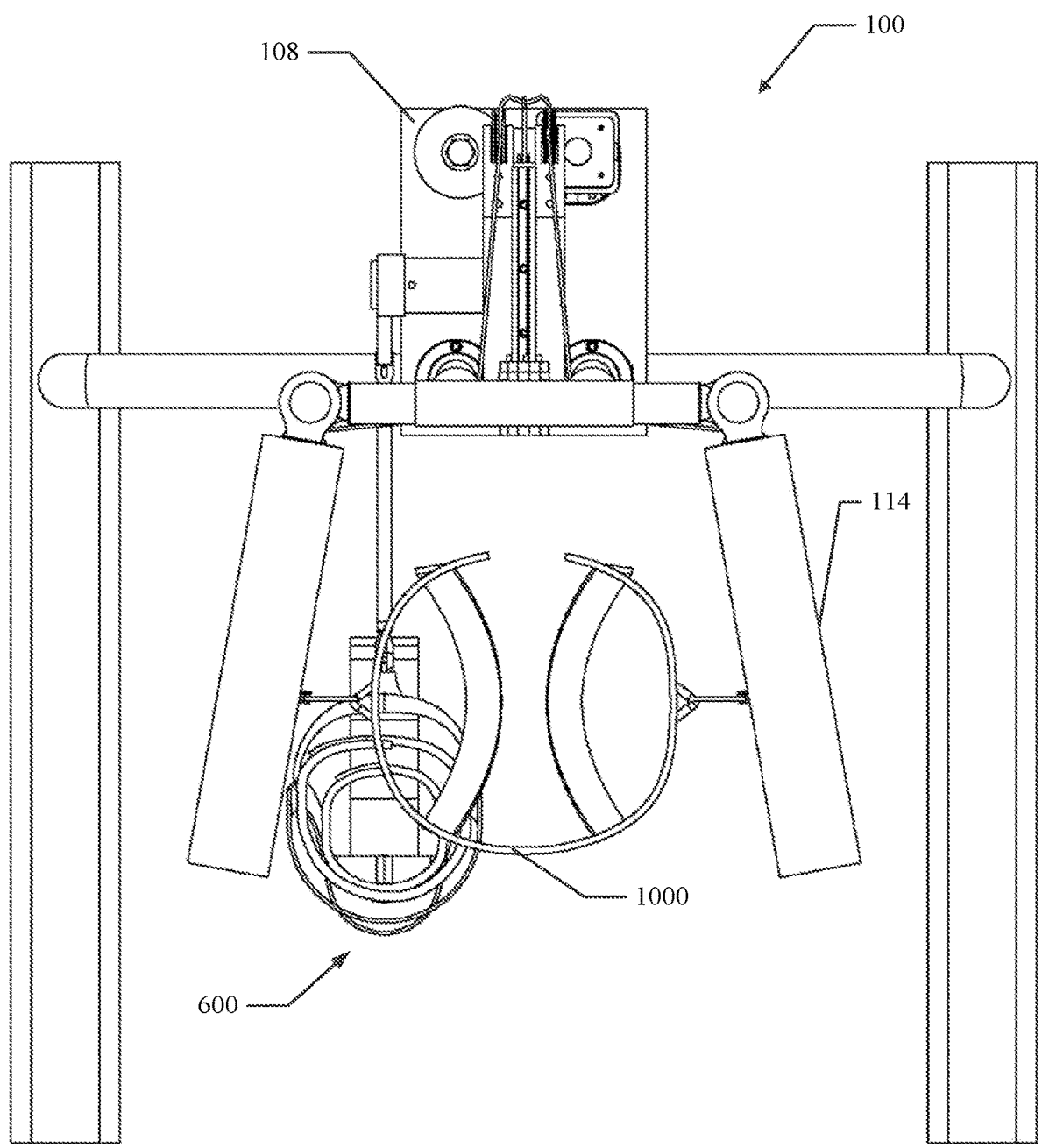
FIG. 14 is a top view of the medical walker, brace, and unweighting harness of FIG. 10.
Figure 15:
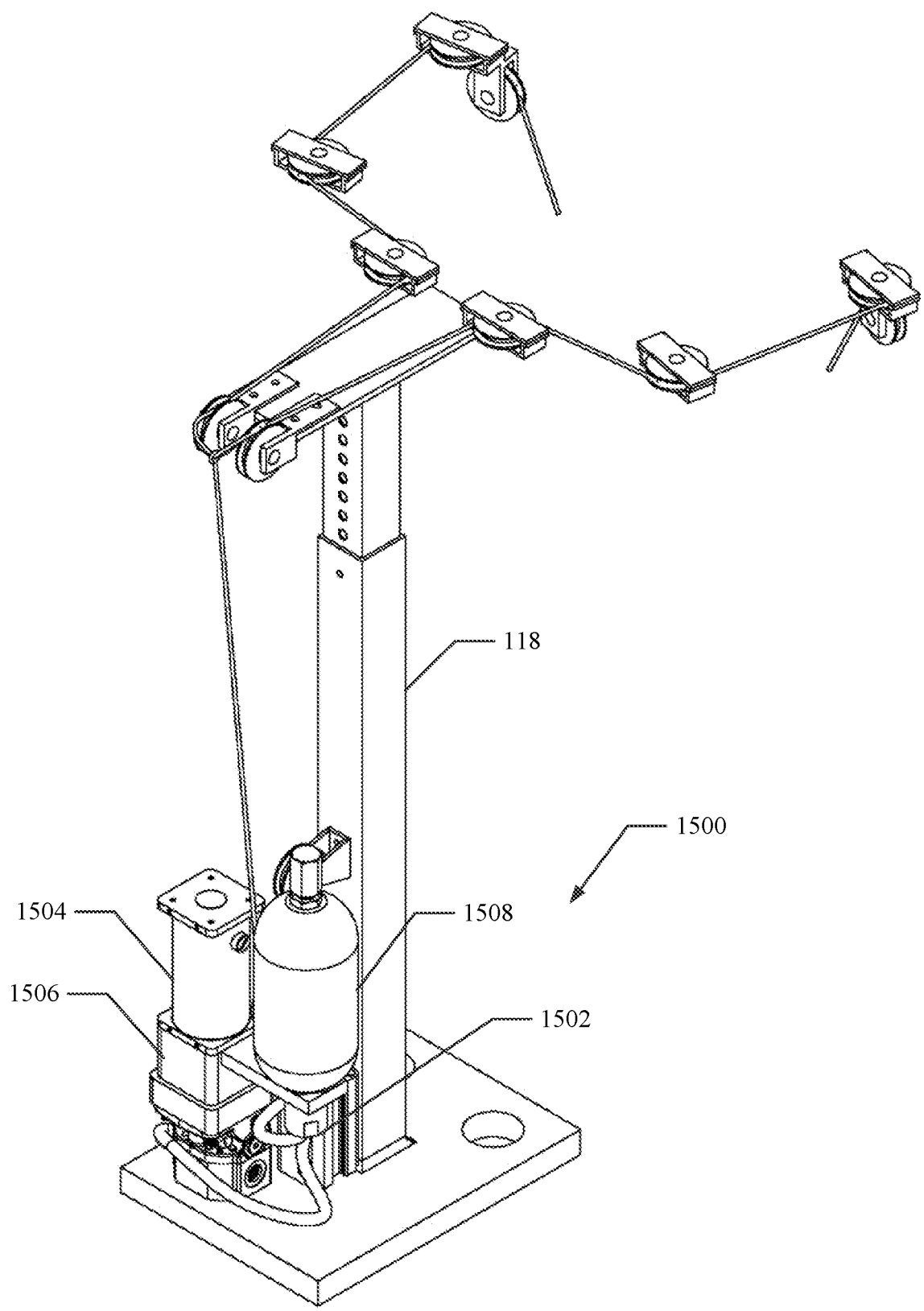
FIG. 15 is a perspective view of an embodiment of a hydraulic unweighting system.
Figure 16:
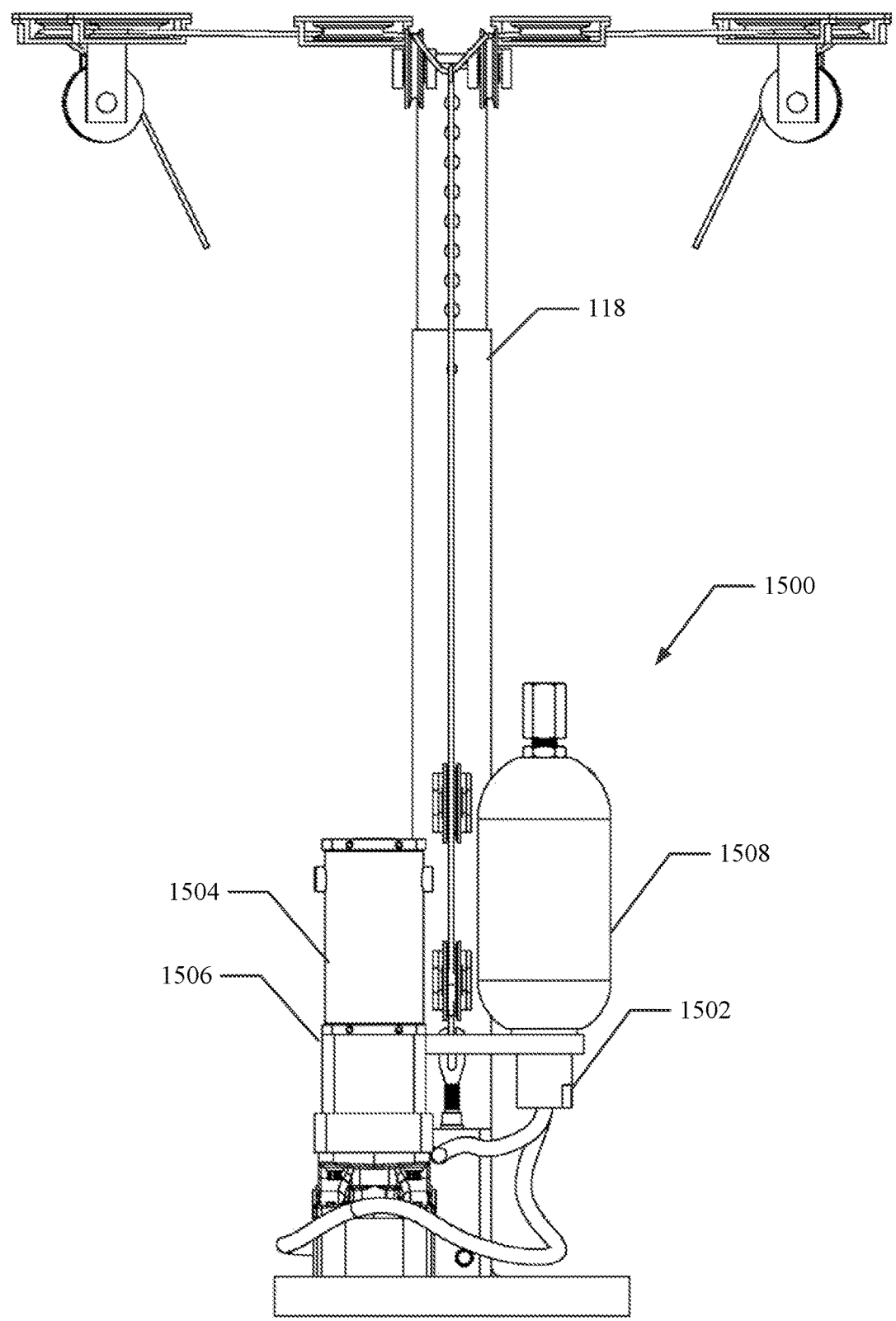
FIG. 16 is a front view of the hydraulic unweighting system of FIG. 15.
Figure 17:
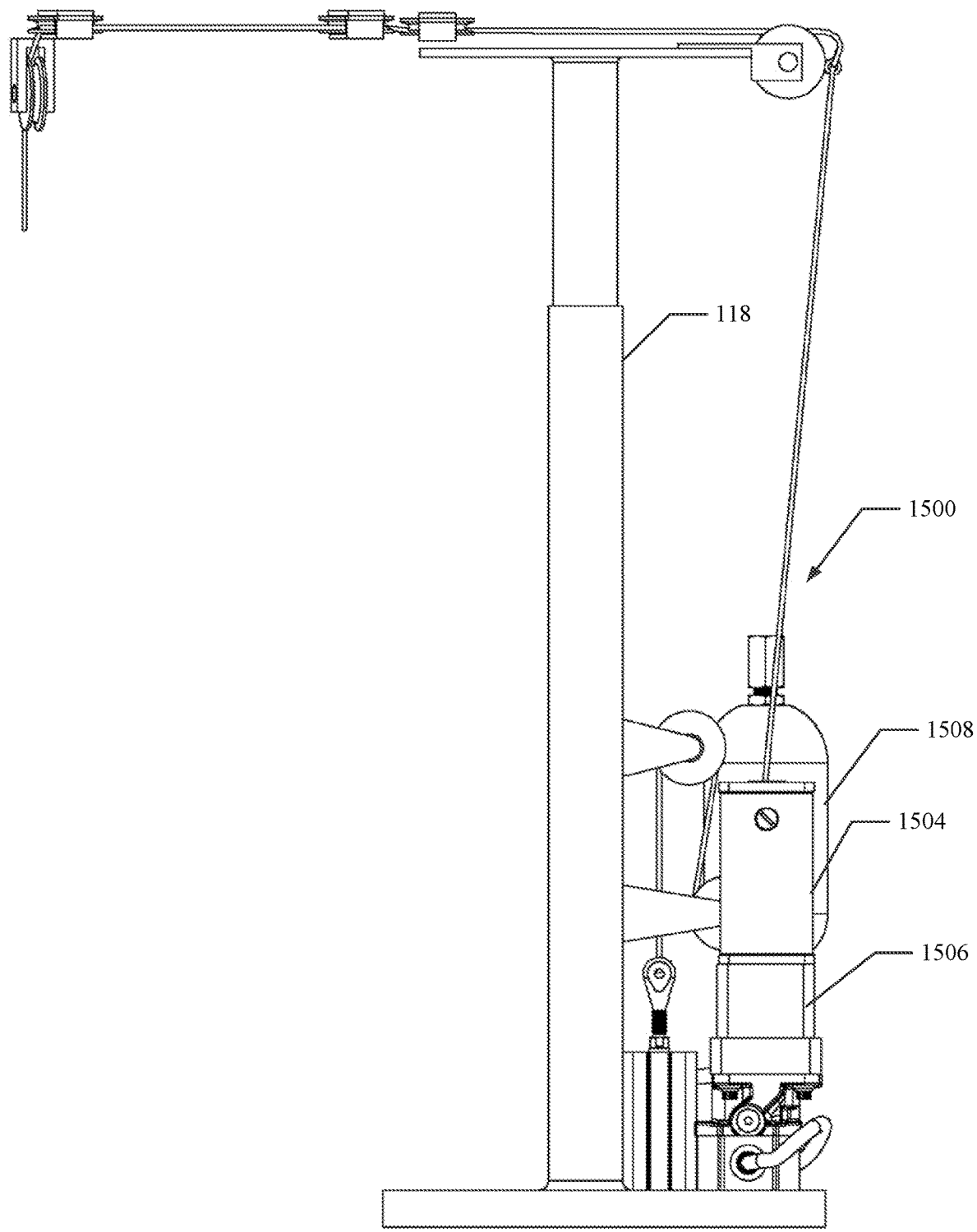
FIG. 17 is a right side view of the hydraulic unweighting system of FIG. 15.
Figure 18:
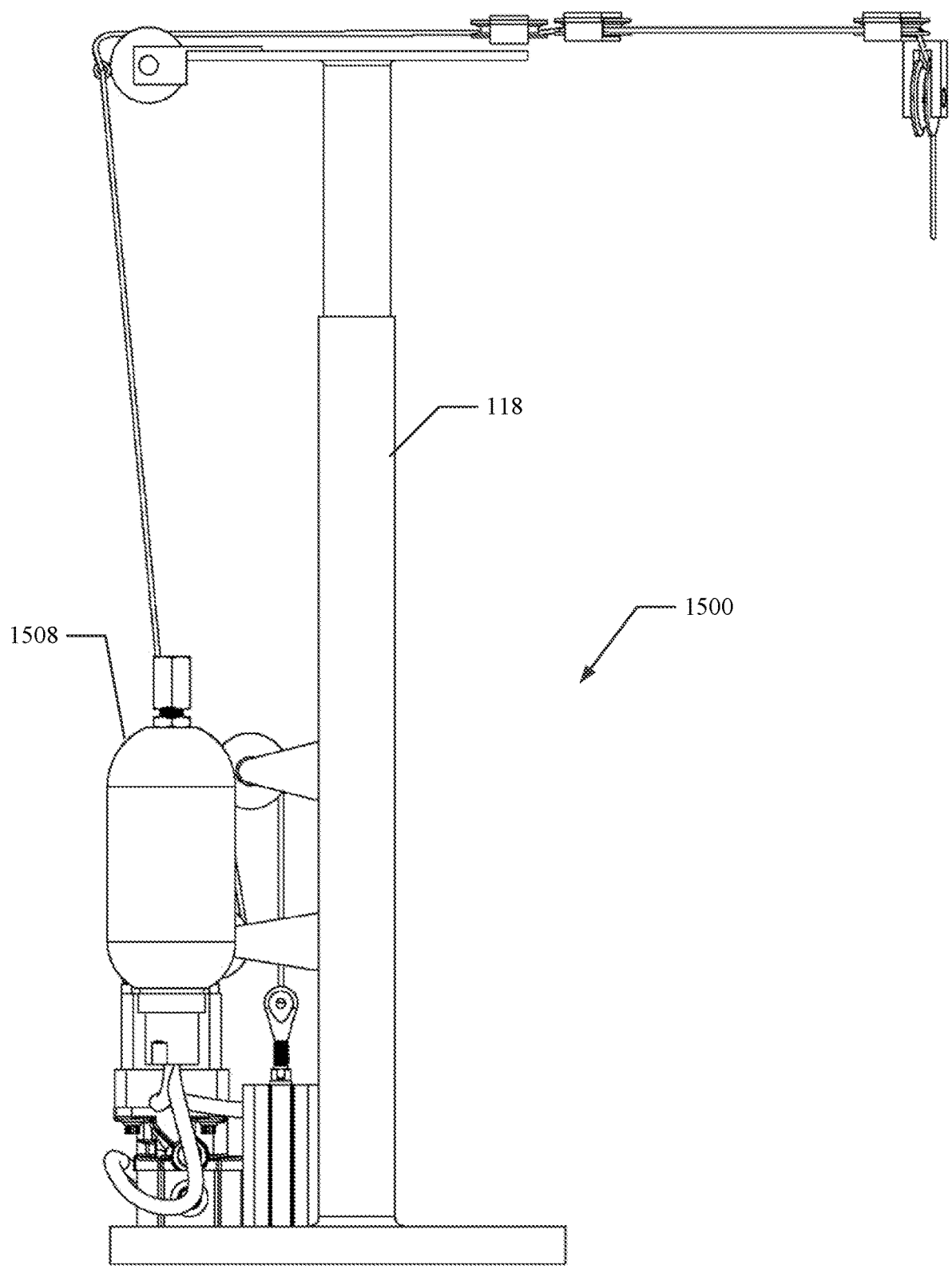
FIG. 18 is a left side view of the hydraulic unweighting system of FIG. 15.
Figure 19:
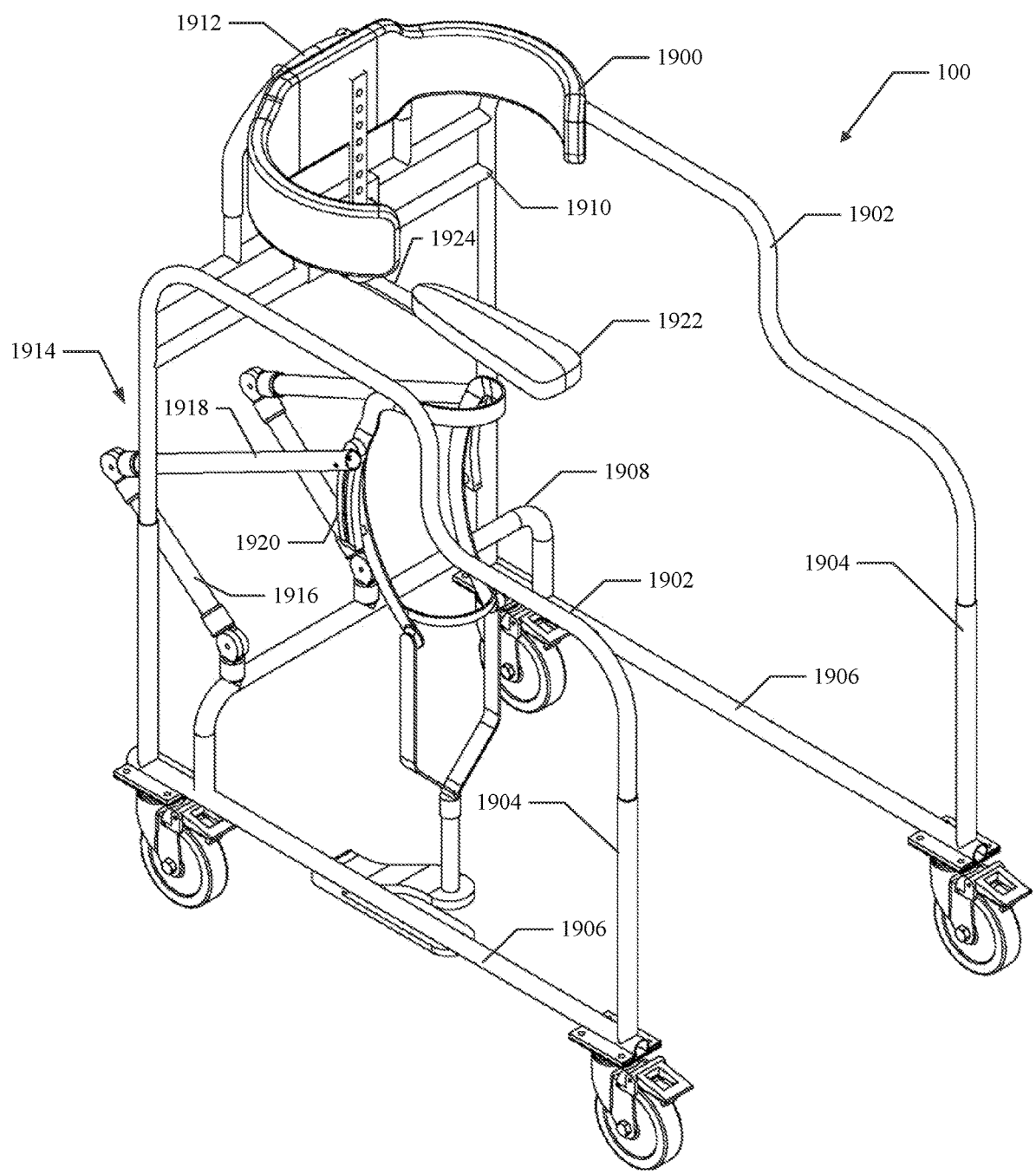
FIG. 19 is a perspective view of another embodiment of the medical walker.
Figure 20:
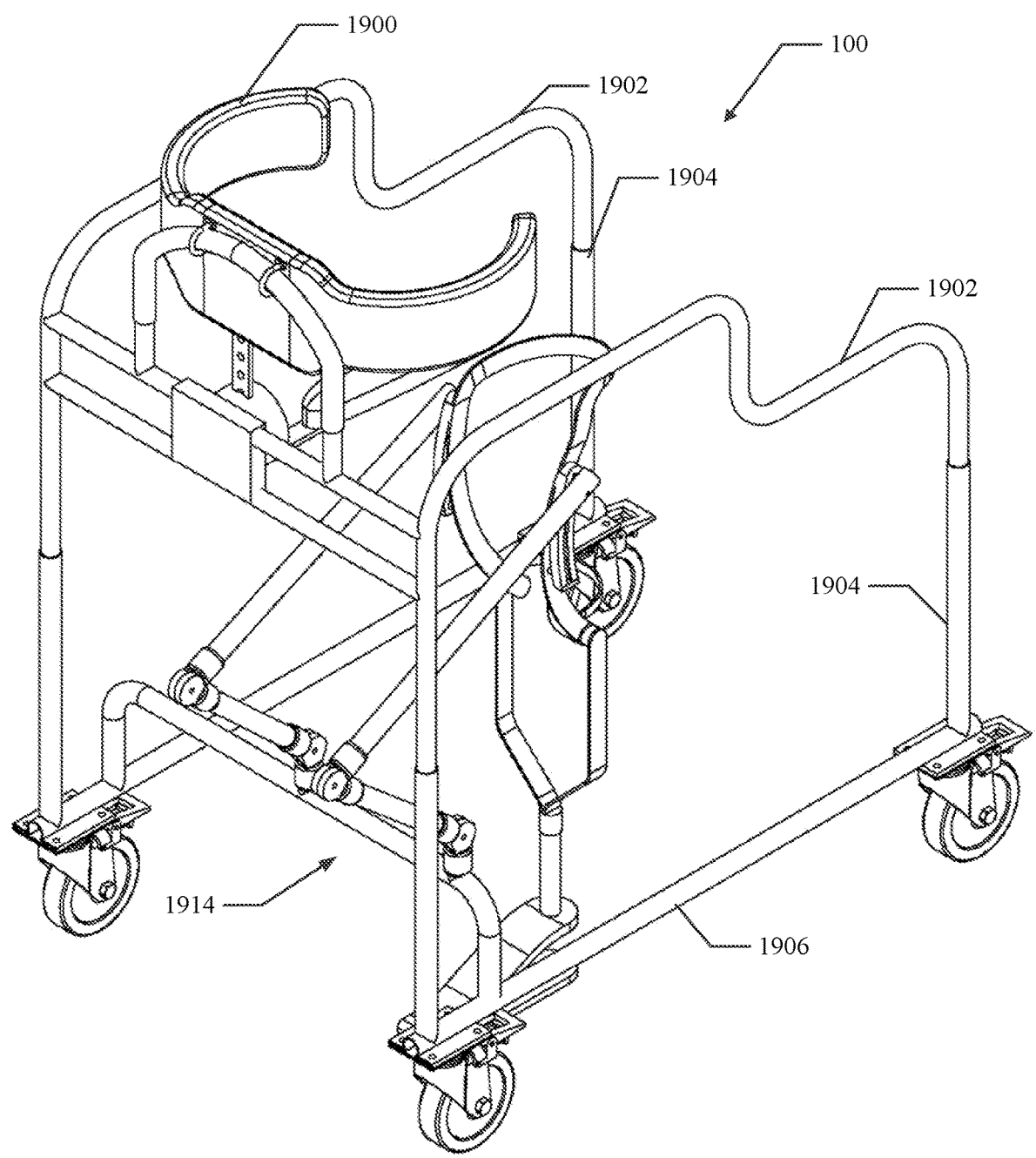
FIG. 20 is an alternate perspective view the medical walker of FIG. 19.
Figure 21:
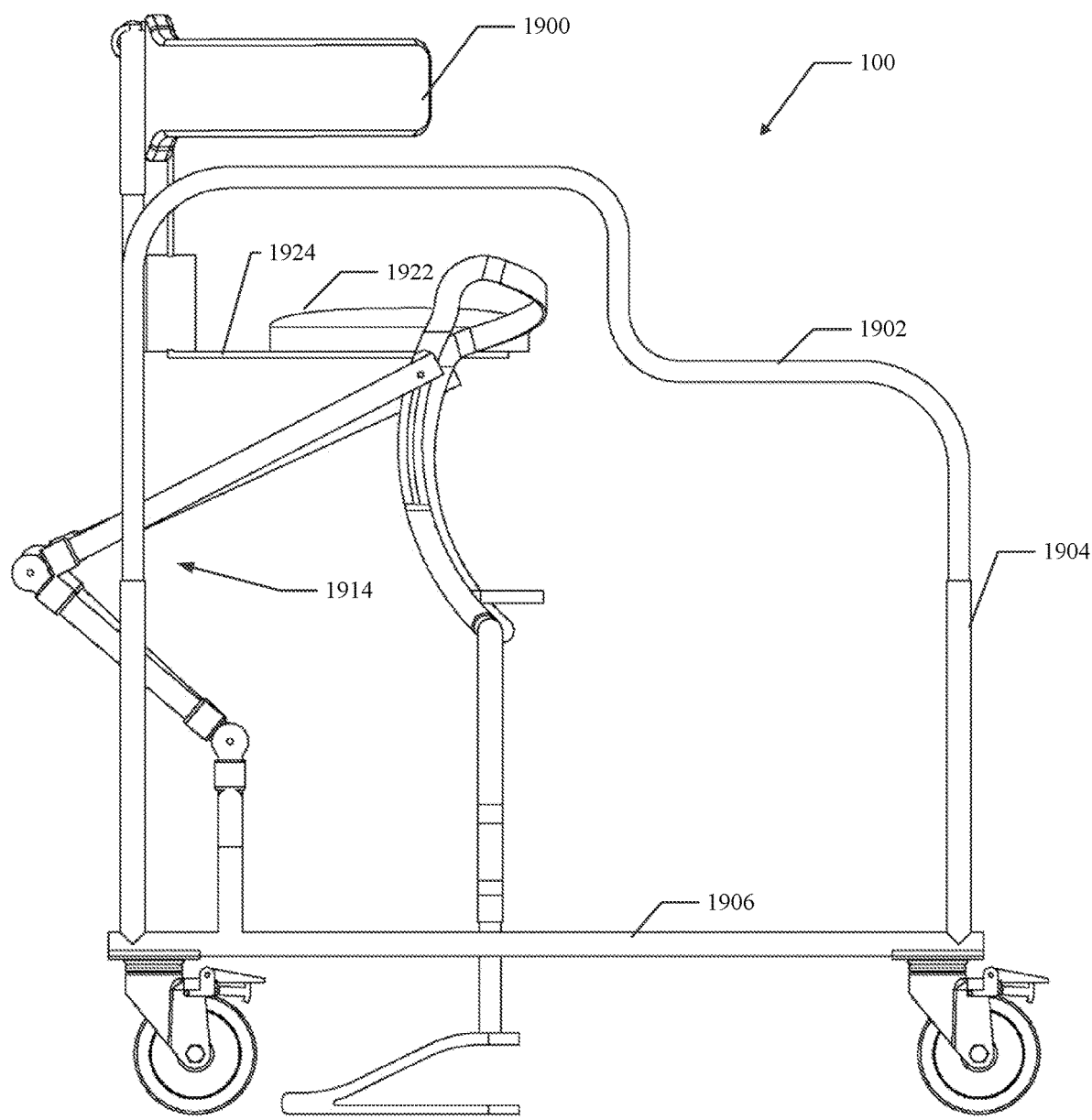
FIG. 21 is a left side view of the medical walker of FIG. 19.
Figure 22:
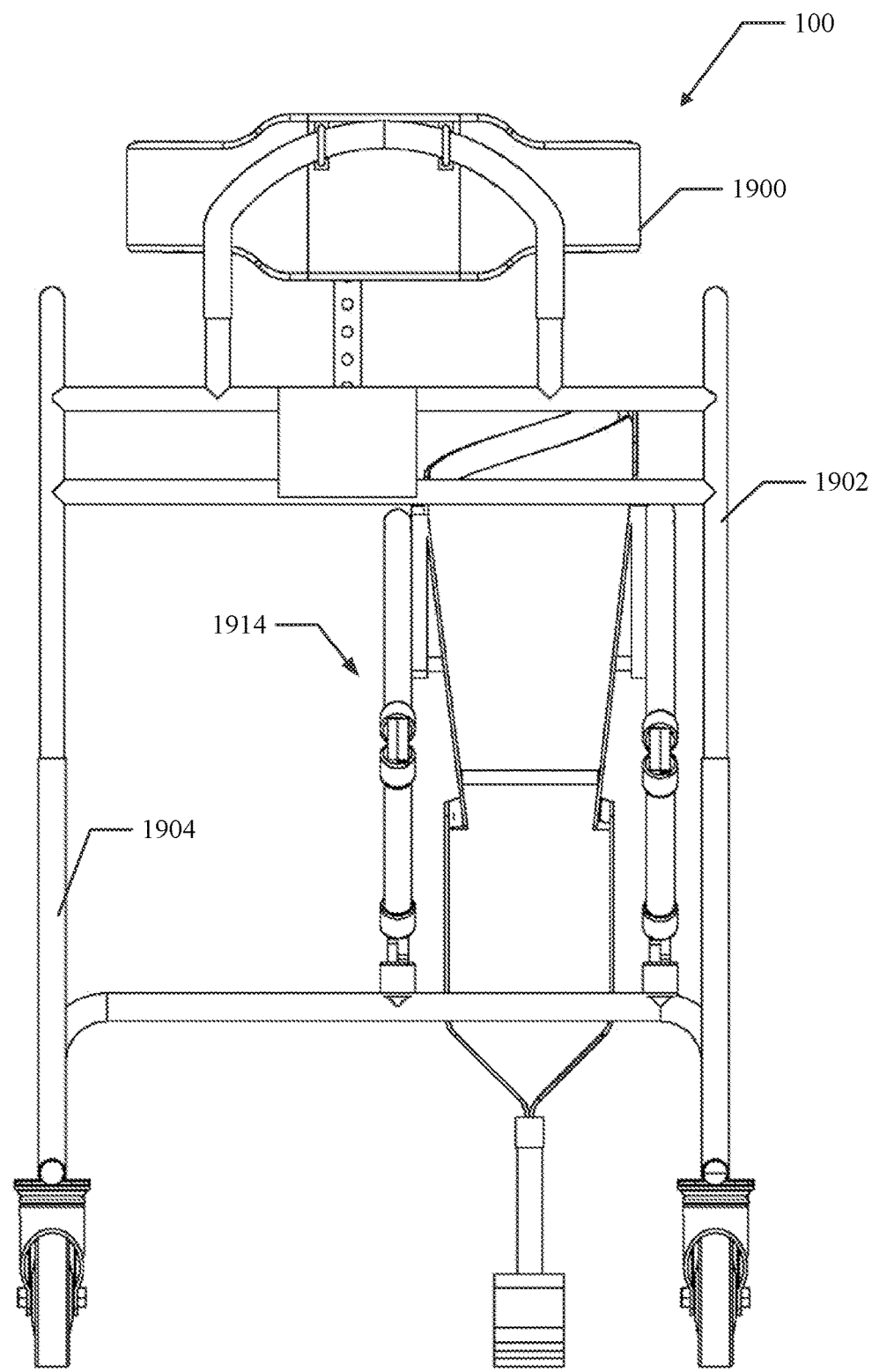
FIG. 22 is a front view of the medical walker of FIG. 19.
Figure 23:
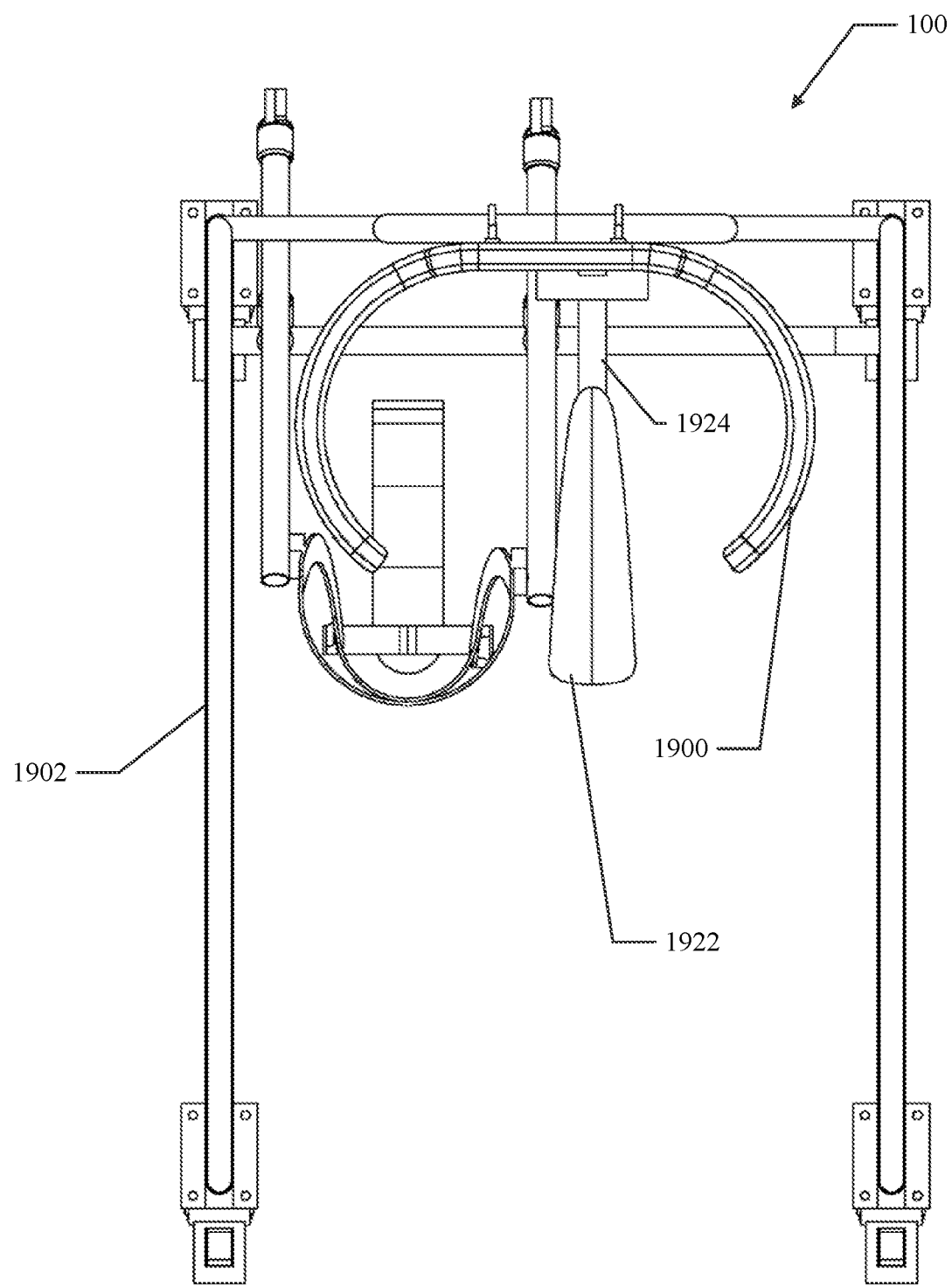
FIG. 23 is a top view of the medical walker of FIG. 19.

Referring now to FIGS. 9A-9C, the swing linkage 604, connected to the customizable leg brace 600 via the yoke 606, guides the movement of the compromised limb in a normal walking motion during use. When the patient takes a step using the compromised limb the patient rotates the limb forward, kicking out the brace 600 in the same manner as a patient would if wearing a prosthetic limb, as illustrated in FIG. 9A. The swing linkages 604 of the compromised limb gait system 106 form an acute angle and the brace 600 rotates relative to the yoke 606. When the patient steps forward and places weight on the limb, the compromised limb in the brace 600 is nearly vertical, as illustrated in FIG. 9B. The swing linkages 604 of the compromised limb gait system 106 form a less acute angle and the brace rotates until it is approximately perpendicular to the yoke 606. As the patient transfers weight off the compromised limb, raising the limb, the swing linkages 604 of the compromised limb gait system 106 form nearly a right angle and the upper swing linkage 604 comes into contact with the hard stop 608, as illustrated in FIG. 9C. This indicates to the patient that it is time to begin the next step in the simulated gait motion. As the patient continues to walk, the patient kicks the brace 600 and compromised limb out again, as illustrated in FIG. 9A, and repeats the cycle. This guides the compromised limb to move in a manner that approximates a normal walking motion and that achieves the angle mechanics of a healthy gait cycle. The swing linkages 604 and yoke 606 prevent lateral motion, encouraging compromised limb to move in a natural manner.

Brace

In embodiments depicted in FIGS. 6-14, the leg brace 600 can be customized to snugly receive the patient's compromised limb. When the walker 100 is in use, the upper end of the leg brace 600 is attached the patient's upper thigh, and in the case of an amputee, the lower end of the leg brace 600 extends beyond the end of the compromised limb to approximate the limb with a fitted prosthetic. Attaching the brace 600 above the amputation protects the wound caused by the amputation from experiencing pressure. In the depicted embodiment, the brace 600 shown is for a patient with an amputation above the knee. However, in an alternative embodiment, the customizable leg brace 600 could attach lower on the compromised limb or extend over a greater surface area of the limb. For example, in the case of a patient with a below the knee amputation, the customized brace 600 could be designed the support the compromised limb below the knee, attaching either above or below the knee joint. In an embodiment, the leg brace 600 is made from a sturdy yet flexible material to minimize the chance of pressure sores on the compromised limb. In the case of a patient that is monoplegic or has reduced function in their compromised limb, but is not an amputee, embodiments of the leg brace 600 can be attached to the compromised limb and can extend from the thigh to the foot of the patient or any portion thereof. In this embodiment, the leg brace 600 can either support and direct movement of the knee or ankle joints, or fix those joints in place. The customizable leg brace 600 may be removed from the walker 100 to allow the patient to attach the customizable leg brace 600 on his or her compromised limb before entering the walker 100.

The embodiments of the leg brace 600 depicted in FIGS. 6-14, 19-24 also illustrate a pseudo-foot 614 attached to the bottom of the customizable leg brace 600. In embodiments, the pseudo-foot 614 is an extension suspended at the bottom of the leg brace 600, and capable of mimicking the movement of the eventual prosthetic limb and/or supporting the brace 600 and compromised limb. The pseudo-foot 614 moves in the same manner as a prosthetic limb, allowing the patient to practice placement of the foot while using the walker 100. In embodiments, the leg brace 600 includes a passive knee joint having a hinge that allows the pseudo-foot 614 to swing freely from the bottom of the leg brace 600. When using the device, the patient's muscles will exert force so that the pseudo-foot 614 will make contact with the ground at times corresponding with a natural walking motion, thus allowing the patient to train to simulate a natural gait motion and activate the muscles utilized during a natural gait motion.

Unweighting System

Referring to FIGS. 10-14, in embodiments, the unweighting system 108 comprises a harness 1000, a series of pulleys and cables 1002, and an adjustable fastener 1004 that attaches a cable to the wheeled frame 102. As shown, the harness 1000 is suspended by the pulleys and cables 1002 from the upper body support 104. The harness 1000 allows the patient to move in a full range of proper walking motion and facilitates proper positioning of the pelvis for a natural gait motion. In the illustrated embodiments, the harness 1000 is similar to a conventional climber's harness, fastening around the waist and legs of the patient while leaving free range of motion. The series of pulleys and cables 1002 allows for the harness 1000 to move vertically and horizontally throughout the simulated gait motion without interfering with the movement of the patients lower limbs. The fastener, connecting a cable to the frame 102, can be implemented in several different ways. For example, in an aspect, the fastener 1004 can be a simple hook or fixed attachment that suspends the harness 1000 at a fixed position, or the fastener 1004 can be adjustable to control the height of the harness 1000. In other aspects, the fastener 1004 can be spring-biased and provide flexible support for the patient.

Turning now to FIGS. 15-18, a hydraulic system 1500 capable of controlling the tension on and displacement of the cables suspending the harness 1000 is shown. In an aspect, the cables suspending the harness 1000 can be attached to a piston cylinder 1502 controlled by a hydraulic system 1500. In embodiments, the hydraulic system 1500 comprises an electric motor 1504, a hydraulic pump 1506, a piston cylinder 1502, and a bladder accumulator 1508. The electric motor 1504 powers the hydraulic pump 1506, where the hydraulic pump 1506 directs hydraulic fluid into the bladder accumulator 1508 and into the piston cylinder 1502. The flow of hydraulic fluid into the piston cylinder 1502 changes the pressure in the piston cylinder 1502 therefore controlling the pulling force of the piston cylinder 1502 and allows the unweighting system 108 to be adjustable and to react to changes in the force exerted on the harness 1000 by the patient during the simulated gait motion. The hydraulic fluid directed into the bladder accumulator 1508 supplies a constant pressure to both the piston cylinder 1502 and the hydraulic pump 1506 thus maintaining a constant pressure throughout the hydraulic system 1500.

Additional Embodiments of the Walker

Turning now to FIGS. 19-23, another embodiment of the walker 100 is depicted. In this embodiment, the illustrated frame 102 comprises a pair of hand bars 1902 connected to vertical poles 1904. A pair of horizontal bars 1906 connect the vertical poles 1904, and one or more crossbars provide stability. The resulting frame 102 is roughly U-shaped. The hand bars 1902 are on the left and right sides of the walker 100, and when in use, the patient is positioned in between the hand bars 1902. The hand bars 1902 are attached to the vertical poles 1904 and extend parallel to the direction of motion of the walker 100. The hand bars 1902 are positioned at approximately at the height of the patient's hips. The patient may use the hand bars 1902 for assistance in standing up from a seated position to a standing position for using walker 100. The hand bars 1902 therefore are, in one aspect, sufficiently strong to support the weight of the patient. At both ends, the hand bars 1902 attach to the vertical poles 1904. In other embodiments, configuration of the elements making up the support structure 118 may differ, while still allowing for the unweighting system 108 (shown in this embodiment as a seat 1922) to be mounted at pelvic height and the upper body support 104 (shown in this embodiment as an abdominal support 1900) at upper body height.

In the embodiment depicted in FIGS. 19-23, the horizontal bars 1906 and vertical poles 1904 are connected though a plurality of crossbars, including a lower crossbar 1908 and two middle crossbars 1910. The lower crossbar 1908 attaches to the horizontal bars 1906 at the anterior end of the horizontal bars 1906, increasing stability without interfering with the stride of a patient using the walker 100. In the depicted embodiment, the lower crossbar 1908 is positioned slightly above the horizontal bars 1906 and is connected to the horizontal bars 1906 by two small vertical segments. This reduces the likelihood that the patient's leg or the leg brace will come into contact with the lower crossbar 1908 when the walker 100 is in use. In the depicted embodiment, part of the compromised limb gait system 106 is attached to and supported by the lower crossbar 1908. For this reason, the lower crossbar 1908 is, in one aspect, sufficiently strong to support the weight of the compromised limb, the customizable leg brace 600, and the compromised limb gait system 106. In other embodiments, configuration of the crossbars may differ, or an alternative to crossbars, such a solid front, may be present while still allowing for the unweighting system 108 to be mounted at pelvic height and the upper body support 104 at upper body height.

As shown, the vertical poles 1904 can be connected by the one or more middle crossbars 1910 at the upper end of the vertical poles 1904. Here, the two middle crossbars 1910 run horizontally between the upper ends of the vertical poles 1904 and support the unweighting system 108 approximately at the height of the patient's hips. In embodiments, the middle crossbars 1910 may be adjusted so that they are positioned lower or higher on the vertical poles 1904, which allows the unweighting system 108 to be raised or lowered. Raising or lowering the unweighting system can adjust the amount of weight placed on the patient's legs as well as allowing for customization based upon the patient's height. In other embodiments, the unweighting system 108 may be connected to the middle crossbars 1910 with a mechanism that allows the unweighting system 108 to be positioned higher or lower with respect to the middle crossbars 1910, adjusting the height and the amount of weight placed on the patient's legs. The middle crossbars 1910 are, in one aspect, sufficiently strong to support the weight the patient places on the unweighting system 108 and weight of the unweighting system 108 itself.

In the depicted embodiment, an upper crossbar 1912 connects to one of middle crossbars 1910 and attaches to the upper body support 104—in this embodiment, an abdominal support 1900. In embodiments, the height of the upper crossbar 1912 and/or position of upper body support 104 is adjustable. This allows the upper body support 104 to be positioned at the correct height to support a patient's upper body, allowing the patient to have a natural, upright posture when using the walker 100. The vertical poles 1904 and upper crossbar 1912 are, in one aspect, of sufficient strength to support the weight the patient places on the upper body support 104 and the weight of the upper body support 104 itself.

In an embodiment, the abdominal support 1900 is connected to the frame 102 of the walker 100 by the upper crossbar 1912. In other embodiments, the abdominal support 1900 may be connected to the frame 102 in different ways, while still allowing for the abdominal support 1900 to be mounted at the patient's abdominal height. In embodiments, the height of the frame 102 can be adjusted so that the abdominal support 1900 is raised or lowered based upon the height of the patient's abdomen, allowing the patients of different heights each to have a natural, upright posture when using the device.

In another embodiment, the compromised limb gait system 106 comprises two, parallel arms 1914, each including a lower portion 1916 and an upper portion 1918, as shown in FIGS. 19-24C. The lower portion 1916 connects to the lower crossbar 1908 with an adjustable joint that allows the lower portion 1916 to rotate forward or backward parallel to the direction of movement of the walker 100. The upper portion 1918 connects to the lower portion 1916 with an adjustable joint that allows the upper portion 1918 to bend with respect to the lower portion 1916 within the same plane that the lower portion 1916 rotates. The upper end of the upper portion 1918 connects to the customizable leg brace 600. The adjustable joints allow the customizable leg brace 600 to be raised or lowered to the height of the patient's compromised limb while keeping the customizable leg brace 600 aligned properly in the horizontal plane. While being adjusted, the adjustable joints are loose so that the arms 1914 may move freely. When in use, the adjustable joints can be tightened so that the arms 1914 are fixed in place.

Figure 24A:
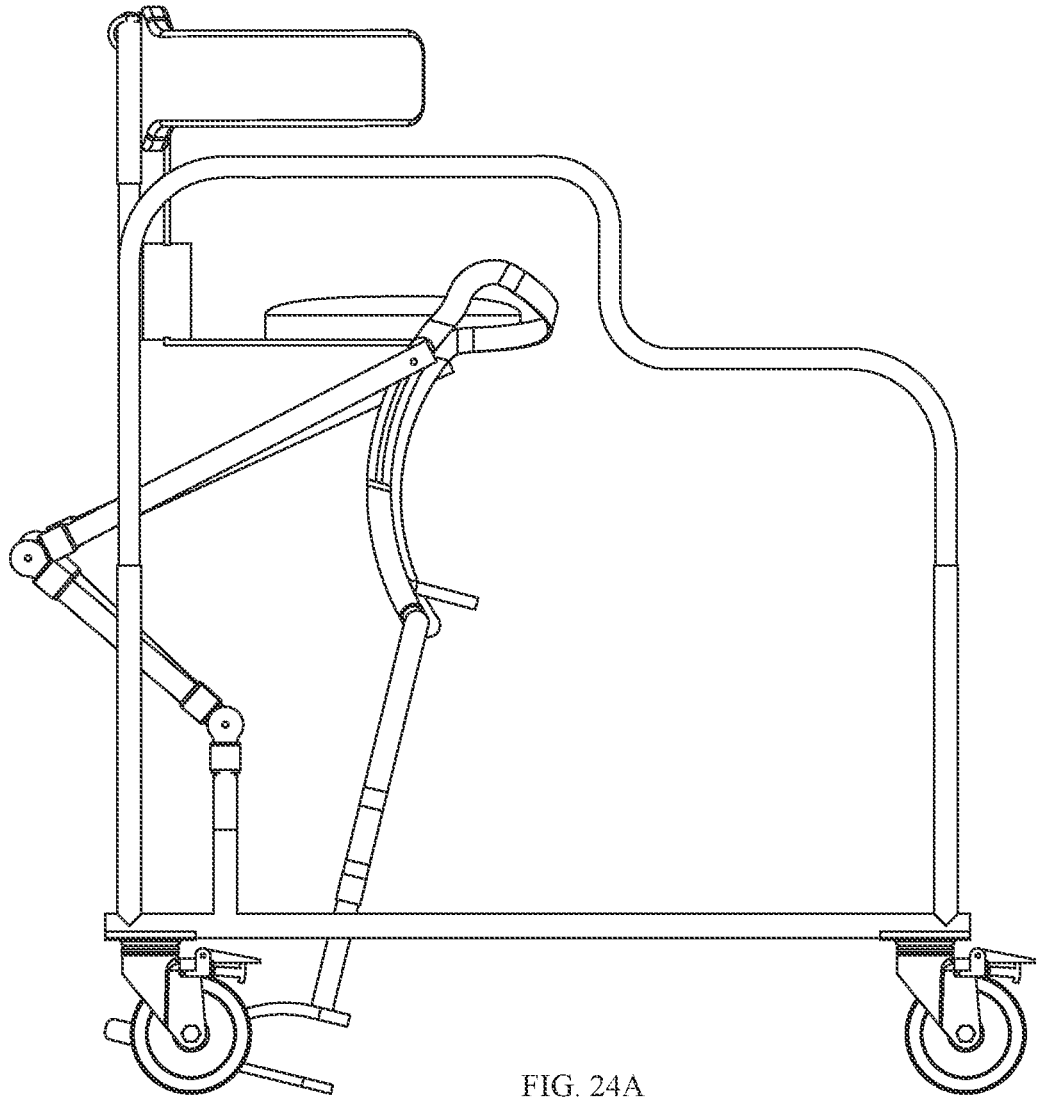
FIG. 24A is a left side view of an embodiment of the medical walker where the brace is in a heel strike position.
Figure 24B:
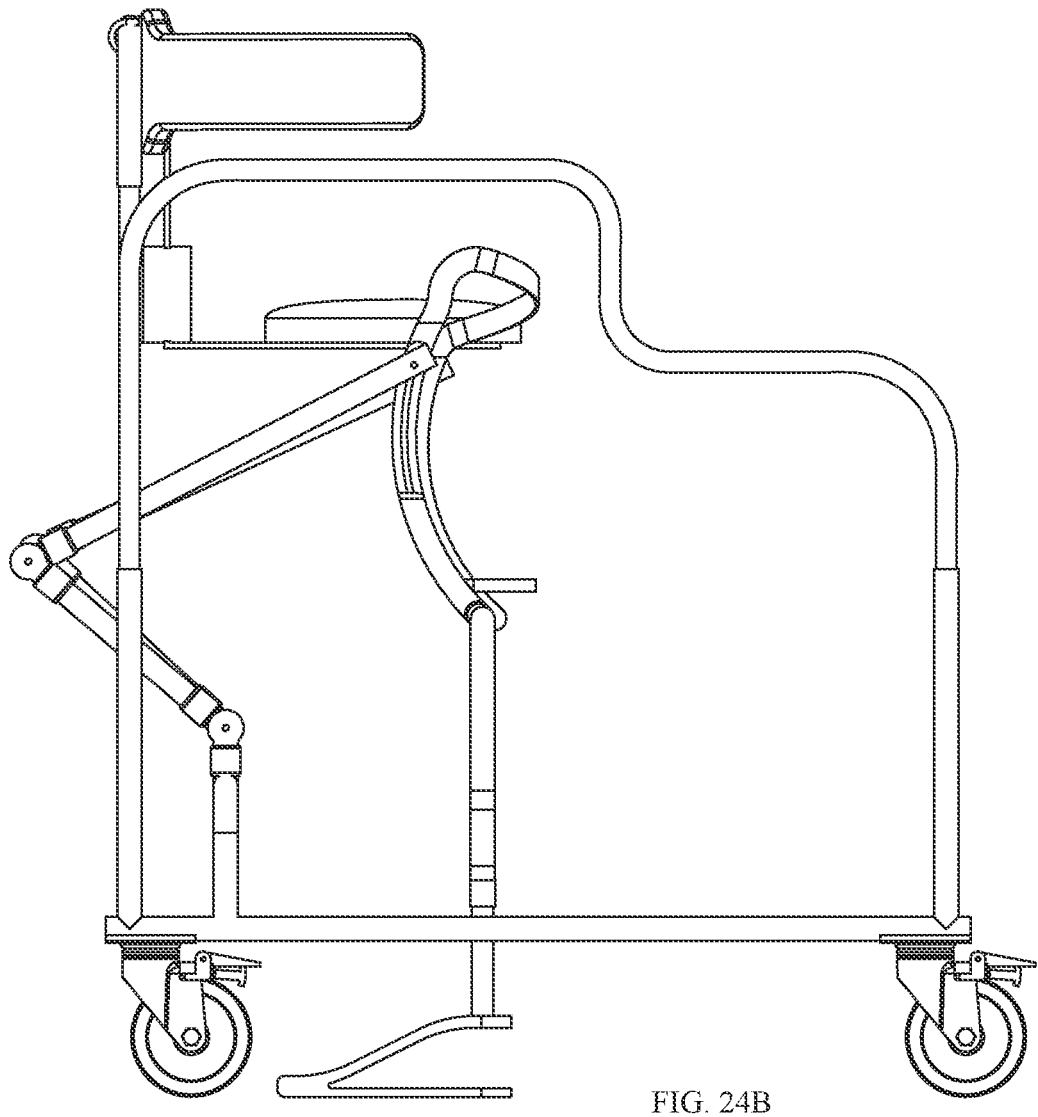
FIG. 24B is a left side view of an embodiment of the medical walker where the brace is in a mid-stride position.
Figure 24C:
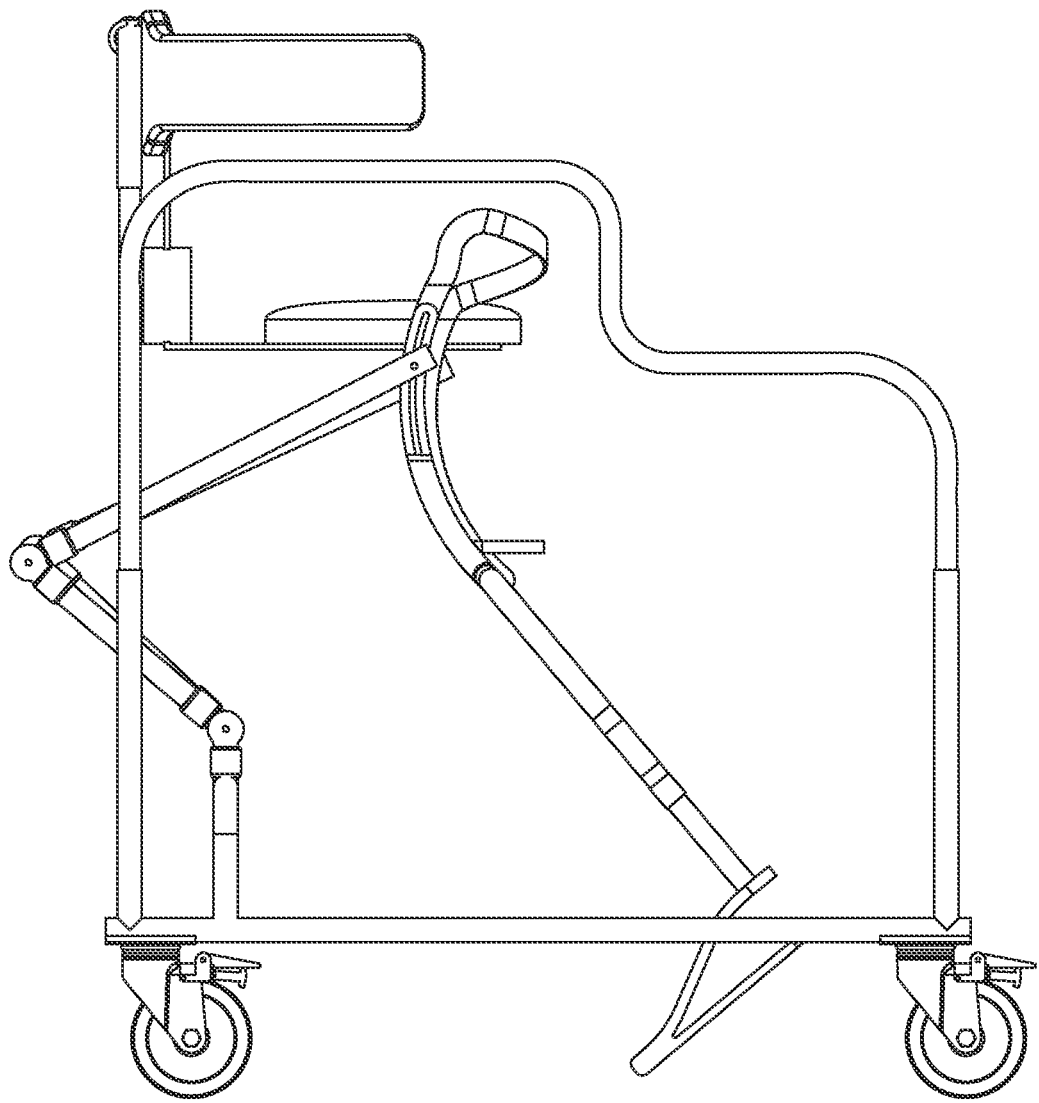
FIG. 24C is a left side view of an embodiment of the medical walker where the brace is in a toe off position.

In the embodiment depicted in FIGS. 19-24C, the arms 1914 are connected to the leg brace 600 via a set of tracks 1920, one track 1920 on each side of the customizable leg brace 600, such that the tracks 1920 guide the movement of leg brace 600, and therefore the compromised limb, in a normal walking motion during use. When the patient places weight on the limb, the compromised limb gait system 106 connects to the top of the track, as illustrated in FIG. 24B. As the patient transfers weight off the compromised limb, raising the limb, the connection between the compromised limb gait system 106 slides along the track 1920 towards the bottom of the track 1920, as illustrated in FIG. 24C. As the patient continues to walk, weight returns to the compromised limb, and the connection between the compromised limb gait system 106 slides back along the track 1920 to the top of the track 1920, as in FIG. 24A. In addition to movement of the end of the arms 1914 along the track 1920, the tracks 1920 rotate with respect to the end of the arms 1914. This guides the compromised limb to move in a normal walking motion that achieves the angle mechanics of a healthy gait cycle.

In the embodiment depicted in FIGS. 19-23, the unweighting system 108 is attached to the middle crossbars and extends towards the posterior of the walker 100. In this embodiment, the unweighting system 108 comprises a seat 1922 and a seat link 1924 attaching the seat 1922 to the frame 102 of the walker 100. During use of the walker 100, the patient sits upon the seat 1922, which can be ergonomic, but still allows the patient to move in the full range of a proper walking motion. For example, in the illustrated embodiment, the seat 1922 is a bicycle-style seat. The underside of the seat 1922 is fixed to the seat link 1924, connecting the seat 1922 to the frame 102.

In embodiments, the seat link 1924 is attached to the middle crossbars 1910 through a mechanism that allows the unweighting system 108 to be positioned higher or lower with respect to the crossbars, having the effect of allowing the unweighting system 108 to be raised or lowered, and adjusting the amount of weight placed on the patient's legs. In an embodiment, the attachment mechanism is vertically spring loaded, which allows the patient to remain seated on the unweighting system 108 during the natural vertical motion of a proper gait. In an embodiment, the attachment mechanism is also free to slide laterally along the middle crossbars, allowing unweighting system 108 to move along with the natural horizontal motion of a proper gait.

Methods of Use

In an embodiment, to use the walker 100, the patient first places the customizable leg brace 600 on the compromised limb while seated, for example, in a wheelchair. The patient then enters the walker 100 through the open, posterior end. The patient can use the support structure 118 or the upper body support 104 for assistance in moving into a standing position. Next, the patient transfers his or her weight onto the unweighting system 108. In embodiments that include an abdominal support 1900, the patient will at this point move in through the opening in the rear of the abdominal support 1900, so that the abdominal support 1900 may support the patient's sides. If the forearm rest 114 is present, the patient then places his or her arms on the forearm rest 114. Once the patient feels stable, he or she attaches the customizable leg brace 600 to the compromised limb gait system 106. Beginning his first stride, the patient will begin the kicking motion on the side of the compromised limb and progress forward through the force on the solid limb. While the patient activates his or her own muscles, the compromised limb gait system 106 will permit the compromised limb to move in an approximation of their normal gait motion. This enables the leg to move through the proper biomechanics of walking and allows the force of the compromised limb to be absorbed through the thigh and hip. The movement of the unweighting system 108 enables the pelvis to ambulate in the proper motion.

What has been described above includes examples of aspects of the claimed subject matter. It is, of course, not possible to describe every conceivable combination of components or methodologies for purposes of describing the claimed subject matter, but one of ordinary skill in the art may recognize that many further combinations and permutations of the disclosed subject matter are possible. Accordingly, the disclosed subject matter is intended to embrace all such alterations, modifications and variations that fall within the spirit and scope of the appended claims. Furthermore, to the extent that the terms "includes," "has" or "having" or variations in form thereof are used in either the detailed description or the claims, such terms are intended to be inclusive in a manner similar to the term "comprising" as "comprising" is interpreted when employed as a transitional word in a claim.

What is claimed is:

1. A medical walker for use by a user with a compromised limb, comprising:
    a wheeled frame adapted to move along a floor surface and support at least a portion of the user's weight;
    a leg brace configured to attach to the compromised limb of the user; and
    a compromised limb gait system connecting the leg brace to the wheeled frame, wherein a first end of the compromised limb gait system attaches to the leg brace at a point below a hip and proximate to a knee of the comprised limb and a distal, a second end of the compromised limb gait system attaches to the wheeled frame at the front of the wheeled frame and not at a pelvis of the user, wherein the compromised limb gait system is configured to guide the compromised limb through a simulated gait motion.

2. The medical walker of claim 1, wherein the compromised limb gait system comprises:
    a forked yoke that connects the leg brace to the compromised limb gait system, wherein the forked yoke connects to the leg brace on both sides of the user's limb;
    at least one swing linkage, wherein the swing linkage permits movement in substantially a single plane and connects the forked yoke to the wheeled frame; and
    a hard stop, wherein the hard stop limits the rearward motion of the swing linkage.

3. The medical walker of claim 2, wherein the leg brace is configured to conform to the limb of the user and wrap around a circumference of the compromised limb to avoid putting pressure on a surgical site on the compromised limb.

4. The medical walker of claim 3, wherein the leg brace further comprises a pseudo-foot protruding from the bottom of the leg brace that mimics the motion of a foot of a prosthetic limb.

5. The medical walker of claim 4, wherein the pseudo-foot acts as a replacement for a foot of the user.

6. The medical walker of claim 5, wherein the leg brace includes a passive knee joint with a hinge that allows the pseudo-foot to swing from the bottom of the leg brace.

7. The medical walker of claim 1, wherein the compromised limb gait system comprises:
    a plurality of parallel arms, wherein each of the parallel arms connects to the wheeled frame at one end of the arms and connects to the leg brace at the opposite end of the arms; and
    a plurality of channels fixed to the leg brace that allow smooth movement of the leg brace through a normal walking gait when connected to the parallel arms.

8. The medical walker of claim 1, wherein the wheeled frame comprises:
    a wheeled base;
    a support structure protruding upwards from the wheeled base; and
    an upper body support attached to the support structure, wherein the upper body support is configured to support at least a portion of the user's weight and promote an upright posture in the user.

9. The medical walker of claim 8, wherein the upper body support is a forearm rest.

10. The medical walker of claim 9, wherein the forearm rest comprises:
    a left arm rest angled to accommodate the user's left forearm;
    a right arm rest angled to accommodate the user's right forearm;
    a central portion connecting the left arm rest and the right arm rest; and
    a plurality of handles extending vertically from the center portion.

11. The medical walker of claim 8, wherein the upper body support is an abdominal support.

12. The medical walker of claim 1, further comprising an unweighting system attached to the wheeled frame, the unweighting system configured to support at least a portion of the user's body weight.

13. The medical walker of claim 12, wherein the unweighting system is adjustable to change an amount of body weight supported by a user's leg and the compromised limb.

14. The medical walker of claim 13, wherein the unweighting system comprises:
    a seat; and
    a seat link that attaches the seat to the wheeled frame at an adjustable height and allows the seat to move laterally.

15. The medical walker of claim 13, wherein the unweighting system comprises:
    a harness that attaches to the user during use of the medical walker;
    a series of pulleys and cables, where the pulleys and cables suspend the harness from the wheeled frame; and
    a fastener that connects the cables to the wheeled frame.

16. The medical walker of claim 15, wherein the fastener is adjustable by a hydraulic system and the hydraulic system comprises:
- an electric motor;
- a hydraulic pump powered by the electric motor;
- a piston cylinder, wherein the hydraulic pump directs hydraulic fluid to control displacement of the piston cylinder; and
- a bladder accumulator, wherein the hydraulic pump directs the hydraulic fluid into the bladder accumulator and the bladder accumulator supplies a constant pressure to the piston cylinder and the hydraulic pump.

17. A method for using a medical walker by a user with a compromised limb, comprising:
- positioning the medical walker for attachment to a leg brace below a hip and proximate to a knee of the compromised limb, wherein the leg brace is attached to the compromised limb of the user and the medical walker comprises:
  - a wheeled frame configured to move on a floor surface;
  - a leg brace configured to attach to the compromised limb of the user; and
  - a compromised limb gait system connecting the leg brace to the front of the wheeled frame and not at the hips and pelvis of the user, where the compromised limb gait system is configured to guide the compromised limb of the user through a simulated gait motion;
- attaching the leg brace to the compromised limb gait system; and
- walking, wherein the compromised limb moves in a simulated gait motion.

18. The method of claim 17, wherein the wheeled frame comprises:
- a wheeled base;
- a support structure protruding upwards from the wheeled base; and
- an upper body support attached to the support structure.

19. The method of claim 17, wherein the wheeled frame further comprises an unweighting system attached to the wheeled frame.

* * * * *